US 7,638,554 B2

(12) United States Patent
Waleh et al.

(10) Patent No.: US 7,638,554 B2
(45) Date of Patent: Dec. 29, 2009

(54) FLAVANOIDS AS CHEMOTHERAPEUTIC, CHEMOPREVENTIVE, AND ANTIANGIOGENIC AGENTS

(75) Inventors: Nahid Waleh, Palo Alto, CA (US); Nurulain T. Zaveri, Saratoga, CA (US)

(73) Assignee: SRI International, Menlo Park, CA (US)

(*) Notice: Subject to any disclaimer, the term of this patent is extended or adjusted under 35 U.S.C. 154(b) by 146 days.

(21) Appl. No.: 11/404,230

(22) Filed: Apr. 14, 2006

(65) Prior Publication Data

US 2006/0264500 A1 Nov. 23, 2006

Related U.S. Application Data

(63) Continuation-in-part of application No. 10/418,736, filed on Apr. 18, 2003, now Pat. No. 7,329,687, which is a continuation-in-part of application No. 10/126,407, filed on Apr. 18, 2002, now abandoned.

(51) Int. Cl.
*A01N 31/35* (2006.01)
*A01N 43/08* (2006.01)
*C07D 311/92* (2006.01)
*C07D 311/00* (2006.01)

(52) U.S. Cl. .................. 514/455; 514/456; 514/457; 514/458; 549/389; 549/390; 549/392; 549/403

(58) Field of Classification Search ............... 514/455, 514/456, 457, 548; 549/389, 390, 392, 403
See application file for complete search history.

(56) References Cited

U.S. PATENT DOCUMENTS

| | | | |
|---|---|---|---|
| 3,862,176 | A | 1/1975 | Fauran et al. |
| 5,792,789 | A | 8/1998 | Wierzbicki et al. |
| 5,879,592 | A | 3/1999 | Kumar |
| 5,952,391 | A | 9/1999 | Gers-Barlag et al. |
| 5,961,892 | A | 10/1999 | Gemert et al. |
| 6,025,387 | A | 2/2000 | Yoo et al. |
| 6,080,338 | A | 6/2000 | Kumar |
| 6,083,978 | A | 7/2000 | Reed et al. |
| 6,248,264 | B1 | 6/2001 | Clarke et al. |
| 2001/0006978 | A1 | 7/2001 | Bok et al. |
| 2002/0147353 | A1 | 10/2002 | Van der Vijgh et al. |
| 2003/0055056 | A1 | 3/2003 | Bombardelli et al. |

FOREIGN PATENT DOCUMENTS

| | | |
|---|---|---|
| DE | 197 42 025 | 3/1999 |
| EP | 0 370 461 | 5/1990 |
| EP | 0 633 022 | 1/1995 |
| WO | WO 01/03681 | 1/2001 |
| WO | WO 01/17984 | 3/2001 |
| WO | WO 01/21164 | 3/2001 |
| WO | WO 01/21608 | 3/2001 |

OTHER PUBLICATIONS

Aitmambetov et al. (1994), "Synthetic Analogs of Natural Flavolignans. I. New Synthesis of Analogs of Silandrin and Hydrocarpin," *Khim. Prir. Soedin.* 3:351-355.
Coronnello et al., "Cytotoxic activity of 3-nitropyrazolo[5,1-c][1,2,4]benzotriazine derivatives: a new series of anti-proliferative agents," Anti-Cancer Drugs (2005) 16:645-651. (Abstract).
Fomun et al., "Erythrina studies. Part 2. Structure of three novel prenylated antibacterial flavanones, sigmoidins A-C, from Erythrina sigmoidea Hua," J. Chem. Perkin Trans (1986) 1:33-37.
Harvey et al. (1990), "A New Chromone and Flavone Synthesis and Its Utilization for the Synthesis of Potentially Antitumorigenic Polycyclic Chromones and Flavones," *J. Org. Chem.* 55(25):6161-6166.
Hossain (1999), "Synthesis of 3',5',7-trihydroxy-6",6"-dimethylpyrano[2",3" : 4', 5']flavanone," *Indian Journal of Chemistry* 38B:427-430.
Mantha et al., "Targeting the mevalonate pathway inhibits the function of the epidermal growth factor receptor," Clin. Cancer Res. (2005) 11:2398-2407. (Abstract).
Pouget et al. (2000), "Synthesis and Structure of Flavan-4-ols and 4-Methoxyflavans as New Potential Anticancer Drugs," *Tetrahedron* 56 (33):6047-6052 (abstract only).
Pouget et al. (2001), "Flavanoids: Structural Requirements for Antiproliferative Activity on Breast Cancer Cells," *Bioorganic & Medicinal Chemistry Letters* 11(24):3095-3097.
Rao et al. (1972), "Synthesis of Propenones and Their Derivatives as Fungicides and Bactericides," *J. Inst. Chem.* 44 (Pt. 5):151-154 (abstract only).
Wang (2000), "The Therapeutic Potential of Flavonoids," *Exp. Opin. Invest. Drugs* 9(9):2103-2119.

*Primary Examiner*—Janet L. Andres
*Assistant Examiner*—Raymond Covington
(74) *Attorney, Agent, or Firm*—Issac M. Rutenberg; Mintz, Levin, Cohn, Ferris, Glovsky & Popeo, PC

(57) ABSTRACT

Compounds useful as chemotherapeutic, chemopreventive, and antiangiogenic agents are provided. The compounds are flavanoids, including flavanones, flavanols, and chalcones. The compounds have the structure of formula (I)

(I)

wherein $R^1$ through $R^3$ and $R^5$ through $R^{11}$ are defined herein, and $\alpha$, $\beta$ and $\gamma$ are optional bonds, providing that when $\alpha$ is absent, $\beta$ is present, and when $\beta$ is absent, $\alpha$ is present. When $\alpha$ is present, preferred $R^4$ moieties are selected from O, S, NH and $CH_2$, and when $\alpha$ is absent, preferred $R^4$ groups are selected from OH, SH, $NH_2$ and $CH_3$. When $\gamma$ is present, the preferred $R^5$ substituent is O, while when $\gamma$ is absent, the preferred $R^5$ substituent is OH. Pharmaceutical compositions are provided as well, as are methods of synthesis and use.

30 Claims, 4 Drawing Sheets

FLAVANOIDS AS CHEMOTHERAPEUTIC, CHEMOPREVENTIVE, AND ANTIANGIOGENIC AGENTS

CROSS-REFERENCE TO RELATED APPLICATIONS

This is a continuation-in-part of U.S. patent application Ser. No. 10/418,736, filed Apr. 18, 2003, which is a continuation-in-part of U.S. patent application Ser. No. 10/126,407, filed Apr. 18, 2002, the disclosures of which are incorporated by reference herein.

GOVERNMENT RIGHTS

This invention was made in part with government support under grant number DAMD17-03-1-0587 awarded by the Army Medical Research Acquisition Activity. The government has certain rights in this invention.

TECHNICAL FIELD

This invention relates generally to flavanoid compounds, particularly flavanones, flavanols, and chalcones, as therapeutic agents. More specifically, the invention relates to novel flavanones, flavanols and chalcone analogs thereof that are useful in the prevention and treatment of cancer and other hyperproliferative diseases.

BACKGROUND

Cancer is the second leading cause of death in the United States, exceeded only by heart disease. Drugs currently used to treat cancer tend to be toxic at their therapeutic dose levels, commonly causing severe and even life-threatening adverse effects. These adverse effects include serious disorders of the blood, gastrointestinal tract, liver, kidneys, and other organs. Most current anticancer drugs thus have a narrow therapeutic window: the range between the therapeutic dose and the maximum tolerated dose is very small. Due to this toxicity, as well as the fact that most anticancer drugs are administered intravenously, nearly all cancer chemotherapy must be administered in a hospital or clinic. An additional problem with most current cancer chemotherapy is that cancers frequently develop resistance to the drugs, so that recurrence of disease is common.

It is therefore of utmost importance to develop new anticancer agents that are effective in treating drug-resistant cancers, exhibit low toxicity, and have a wide therapeutic window, such that an agent targets diseased tissue while sparing healthy tissue. An ideal anticancer agent would also be easily administrable outside of a clinical setting; orally active compounds would be particularly attractive in this regard. Ideal agents would also be useful prophylactically in patients at risk of developing cancer, in addition to their utility in therapeutic methods. Angiogenesis, the process by which new blood vessels are formed, is essential for many normal physiologic functions, including growth, establishment of the placenta, and wound repair. It is also essential for the growth of cancerous tumors larger than about two mm in diameter (Weidner et al. (1991) *New England J. Med.* 324:1-8). To obtain sufficient nutrients and oxygen, tumors secrete factors that induce the development of new blood vessels that connect the tumor to the surrounding tissue. Once a tumor establishes a system of blood vessels connected to the host organism, a means is provided by which tumor cells can enter the circulation and metastasize to distant sites such as the liver, lung, or bone. If this neovascularization is prevented or destroyed, the tumor will eventually shrink and die. Some of the most promising anticancer compounds in development are antiangiogenic. These compounds include: angiostatin, a polypeptide of approximately 200 amino acids produced by the cleavage of plasminogen, a plasma protein involved in dissolving blood clots; endostatin, a polypeptide of 184 amino acids that is the globular domain found at the C-terminal of Type 18 collagen, a collagen found in blood vessels; and troponin I, a protein found in muscles. Another antiangiogenic compound in development is a monoclonal antibody directed against the vascular integrin anb3. Other experimental compounds are targeted against VEGF. As all of these compounds in development are proteins, they cannot be administered orally, and they may induce allergic reactions. An additional experimental antiangiogenic compound, suramin, has such high systemic toxicity that its utility is severely limited.

Many diseases other than cancer are also associated with pathologic angiogenesis. Ocular neovascularization has been implicated as the most common cause of blindness. In diabetic retinopathy, capillaries formed in the retina invade the vitreous, bleed, and cause gradual loss of vision leading to blindness. In arthritis, newly formed capillaries and other blood vessels invade the joints and destroy cartilage. In psoriasis, angiogenesis is required to maintain the rapid growth and turnover of skin cells. Many other examples of inflammatory disorders and other diseases associated with angiogenesis are known in the art.

Although some antiangiogenic agents are quite active, many of the currently known agents are associated with a number of problems. For example, many of the known antiangiogenic agents exhibit poor bioavailability, result in numerous side effects, have problems with stability, and are difficult to synthesize in an efficient manner.

Endothelial cell proliferation is a key process in angiogenesis. Endothelial cells form the endothelium—a thin layer of cells that lines blood vessels. Angiogenesis relies on the ability of endothelial cells to proliferate in order to form the endothelium of the newly forming vessels. Thus, while the proliferation of endothelial cells is required for normal physiological processes, angiogenesis associated with the growth of a tumor involves the unwanted proliferation of endothelial cells.

Angiogenesis also requires migration of endothelial cells, for example through the extracellular matrix. Cellular migration is undesirable in the context of metastasis and tumor cells; endothelial cell migration is similarly undesirable in the context of pathologic angiogenesis. The migration of endothelial cells is aided by matrix metalloproteinases, which are involved in the degradation of the extracellular matrix. Importantly, the migration of tumor cells is also aided by matrix metalloproteinases. Thus, the inhibition of matrix metalloproteinases represents a potential method for interrupting metastasis.

Methods of treatment which disrupt unwanted proliferation of endothelial cells and/or unwanted migration of tumor cells and/or endothelial cells would be expected to have value in the treatment of angiogenesis, but would also be expected to have value in the treatment of disease processes besides angiogenesis, especially metastasis. Such methods are therefore desirable independently of how effective they are against angiogenesis.

SUMMARY OF THE INVENTION

The present invention is directed to the aforementioned need in the art, and provides novel flavanoids that are potent inhibitors of angiogenesis, and, as such, are useful for treating patients with advanced cancers. The novel compounds provide a number of advantages relative to compounds that are known or currently under consideration as antiangiogenic agents. For example, the present compounds have a very broad therapeutic window, in turn meaning that no toxicity will be seen even at fairly high doses. In addition, the compounds do not give rise to the numerous and debilitating side effects that are associated with many drugs. From a safety standpoint, then, the novel compounds are optimal. Furthermore, the present compounds have fairly simple molecular structures, and may be readily synthesized using straightforward synthetic techniques. Pharmaceutical compositions formulated with the novel compounds are stable and readily delivered, providing excellent bioavailability. This is in sharp contrast to current peptidyl and saccharidic antiangiogenic agents, which are generally difficult to synthesize and obtain in significant quantities, are frequently associated with low bioavailability, and exhibit drug delivery and stability problems.

The invention thus provides novel compounds that are useful as chemotherapeutic, chemopreventive, and antiangiogenic agents. The novel therapeutic agents are flavanoids, including flavanones, flavanols, and chalcones as described below.

In one embodiment, the compounds of the invention are capable of stimulating the endogenous production of inhibitors of metalloproteinases. The compounds may thus be useful in inhibiting unwanted cellular migration.

In one embodiment, a therapeutic compound is provided having the structure (I)

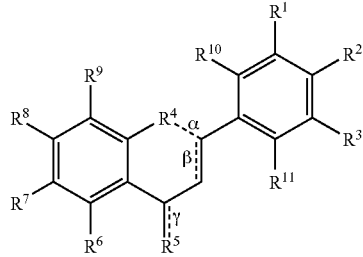

(I)

wherein:

α, β and γ are optional bonds, providing that when α is absent, β is present, and when β is absent, α is present;

$R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;

when α is present, $R^4$ is selected from O, S, $NR^x$, and $CR^yR^z$, and when α is absent, $R^4$ is selected from OH, SH, $NHR^x$, and $CR^yR^zH$, wherein $R^x$, $R^y$, and $R^z$ are hydrogen or alkyl;

when γ is present, then $R^5$ is O, S or $NR^x$;

when γ is absent, then $R^5$ is selected from the group consisting of hydroxyl, acyloxy, sulfhydryl, and $N(R^x)$ wherein the $R^x$ may be the same or different and are as defined previously, and "acyloxy" refers to an ester substituent —O—(CO)—R in which R is substituted or unsubstituted aliphatic, aromatic, or alicyclic;

$R^6$, $R^7$, $R^8$ and $R^9$ may be hydrogen, such that the ring indicated is unsubstituted, or one or more of $R^6$, $R^7$, $R^8$ and $R^9$ may be a nonhydrogen ring substituent (e.g., substituted and/or heteroatom-containing hydrocarbyl, or a functional group), although generally $R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, or $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{10}$ and $R^{11}$ are independently selected from the group consisting of hydrogen, hydroxyl, alkyl, alkoxy, and halo.

The following compounds (II), (III) and (IV) respectively illustrate flavanone, flavanol and chalcone compounds encompassed by formula (I).

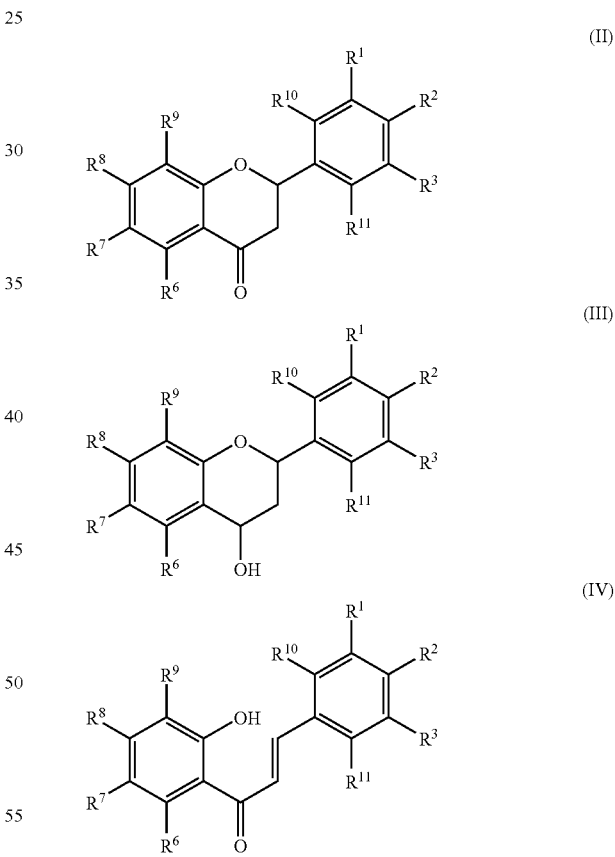

In a further embodiment, methods are provided for synthesizing the compounds of the invention. The methods are straightforward, avoid the use of extreme reaction conditions and toxic solvents, and provide the desired products in high yield.

In another embodiment, the invention encompasses pharmaceutical compositions containing a novel compound as provided herein in combination with a pharmaceutically acceptable carrier. Preferably, although not necessarily, such compositions are oral dosage forms and thus contain a carrier suitable for oral drug administration.

In an additional embodiment, the invention is directed to a method for treating an individual suffering from cancer, comprising administering to the individual a therapeutically effective amount of a novel compound as provided herein. In addition to their general utility as chemotherapeutic agents, the compounds are also useful in chemoprevention and in the treatment of angiogenesis. Therefore, the invention additionally pertains to a method for preventing cancer and to a method for treating a condition, disease or disorder associated with angiogenesis, e.g., cancer, by administering a therapeutically effective amount of a compound of the invention to a patient. Generally, in chemoprevention, the patient will have been identified as being at an elevated risk of developing cancer. Such patients include, for example, those with a family history of cancer or a particular type of cancer, as well as those who have undergone genetic analysis and thereby determined to be genetically predisposed to develop cancer or a particular type of cancer.

In another embodiment, the invention is directed to a method of inhibiting tumor cell invasion through an extracellular matrix in a patient, comprising administering to the patient a therapeutically effective amount of a compound as provided herein.

In another embodiment, the invention is directed to a method of inhibiting the action of a metalloproteinase involved in the breakdown of the extracellular matrix comprising administering to a patient in need thereof an effective amount of a compound as provided herein.

In yet another embodiment, the invention is directed to a method of inhibiting unwanted endothelial cell growth or migration in a patient, comprising administering a compound as provided herein.

In yet another embodiment, the invention is directed to a method of inhibiting unwanted endothelial cell growth or migration in a patient comprising contacting a mammalian endothelial cell with an effective amount of a compound as provided herein.

In still another embodiment, the invention is directed to a method of treating a patient suffering from a condition linked to the breakdown of the extracellular matrix by metalloproteinase and/or to the unwanted proliferation of endothelial cells, comprising administering to the patient a compound as provided herein.

BRIEF DESCRIPTION OF THE DRAWINGS

FIG. 3 provides the results obtained with intraperitoneal injection of the compound, while FIG. 4 provides the results obtained with oral administration.

DETAILED DESCRIPTION OF THE PREFERRED EMBODIMENTS

I. Definitions and Nomenclature

Figure 1:
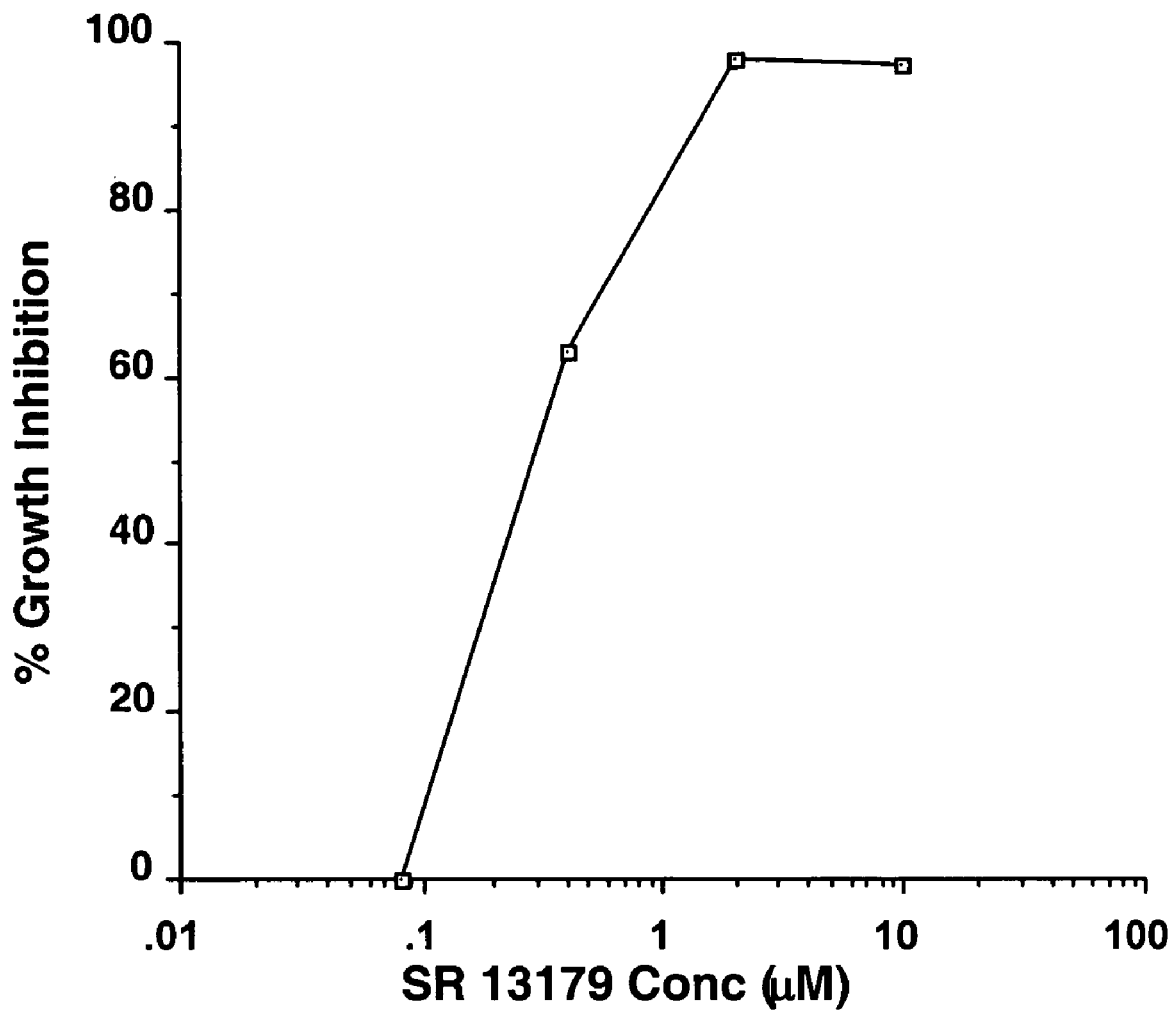
FIG. 1 is a graph showing the growth inhibition of human umbilical vein endothelial cells by a compound of the invention (2-(3,4,5-trimethoxyphenyl)-3,4-dihydro-2H-benzo[h]chromen-4-ol, "SR 13179") using an MTT assay, as described in Example 17.

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "$C_1$-$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkylene" refers to a difunctional linear, branched or cyclic alkyl group, where "alkyl" is as defined above. Alkylene linkages thus include —CH$_2$—CH$_2$— and —CH$_2$—CH$_2$—CH$_2$—, as well as substituted versions thereof wherein one or more hydrogen atoms is replaced with a nonhydrogen substituent. "Heteroalkylene" linkages refer to an alkylene moiety wherein one or more methylene units is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 12 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "aralkyl" refers to an alkyl group with an aryl substituent, wherein "aryl" and "alkyl" are as defined above. Preferred aralkyl groups contain 5 to 20 carbon atoms, and particularly preferred aralkyl groups contain 5 to 12 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "aralkyloxy" refers to an aralkyl group bound through a single, terminal ether linkage. As above, an "aralkyloxy" group may be represented as —O-Alk(Ar) wherein "Alk" is an alkyl group and "Ar" is an aryl substituent. Preferred aralkyloxy groups contain 5 to 20 carbon atoms, and particularly preferred aralkyloxy groups contain 5 to 12 carbon atoms. Aralkyloxy substituents include, for example, benzyloxy, 2-phenoxy-ethyl, 3-phenoxy-propyl, 2-phenoxy-propyl, 2-methyl-3-phenoxypropyl, 2-ethyl-3-phenoxypropyl, 4-phenoxy-butyl, 3-phenoxy-butyl, 2-methyl-4-phenoxybutyl, 4-phenoxycyclohexyl, 4-benzyloxycyclohexyl, 4-phenoxy-cyclohexylmethyl, 2-(4-phenoxy-cyclohexyl)-ethyl, and the like.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, alkoxy, alkenyloxy, alkynyloxy, aryloxy, acyl (including alkylcarbonyl (—CO-alkyl) and arylcarbonyl (—CO-aryl)), acyloxy (—O—(CO)—R, R=alkyl, aryl, allkaryl, etc.), alkoxycarbonyl (—(CO)—O-alkyl), aryloxycarbonyl (—(CO)—O-aryl), halocarbonyl (—(CO)—X where X is halo), carboxy (—COOH), carboxylato (—COO$^-$), carbamoyl (—(CO)—NH$_2$), alkylcarbamoyl (—(CO)—NH-alkyl), arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), primary amino (—NH$_2$), mono- and di-(alkyl)-substituted amino, mono- and di-(aryl)-substituted amino, alkylamido (—NH—(CO)-alkyl), arylamido (—NH—(CO)-aryl), imino (—CR=NH where R=hydrogen, alkyl, aryl, alkaryl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), alkylsulfanyl (—S-alkyl; also termed "alkylthio"), arylsulfanyl (—S-aryl; also termed "arylthio"), alkylsulfinyl (—(SO)—O-alkyl), arylsulfinyl (—(SO)—O-aryl), boryl (—BH$_2$), borono (—B(OH)$_2$), phosphono (—P(O) (OH)$_2$), phosphonato (—P(O)(O$^-$)$_2$), phosphinato (—P(O) (O$^-$)), phospho (—PO$_2$), and phosphino (—PH$_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{12}$ aryl), and $C_5$-$C_{20}$ aralkyl (preferably $C_5$-$C_{12}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase an "optionally present" bond as indicated by a dotted line ----- in the chemical formulae herein means that a bond may or may not be present.

In the molecular structures herein, the use of bold and dashed lines to denote particular conformation of groups follows the IUPAC convention. A bond indicated by a broken line indicates that the group in question is below the general plane of the molecule as drawn (the "β" configuration), and a bond indicated by a bold line indicates that the group at the position in question is above the general plane of the molecule as drawn (the "α" configuration). Single bonds that are not indicated by broken or bold lines may be in either configuration; such bonds may also be indicated by the conventional symbols ——or ∿∿.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a patient with a compound of the invention includes prevention of a particular disorder or adverse physiological event in a susceptible individual as well as treatment of a clinically symptomatic individual by inhibiting or causing regression of a disorder or disease. For example, treatment of a patient by administration of an anti-cancer agent of the invention encompasses chemoprevention as well as chemotherapy and antiangiogenesis.

By the terms "effective amount" or "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. The Novel Flavanoids

The compounds of the invention are flavanoids and analogs thereof, having the structure of formula (I)

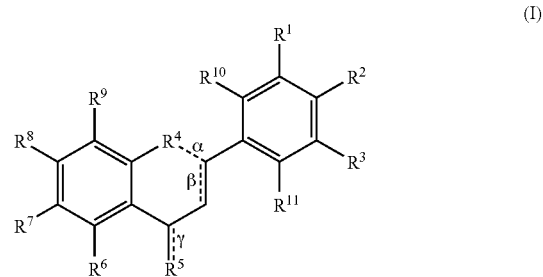

(I)

wherein α, β and γ are optional bonds, providing that when α is absent, β is present, and when β is absent, α is present, and the various substituents are defined as follows.

$R^1$, $R^2$ and $R^3$ are independently selected from the group consisting of: hydroxyl; sulfhydryl; halo; alkoxy, preferably $C_1$-$C_6$ alkoxy, such as methoxy and ethoxy, with methoxy preferred; aryloxy, preferably $C_5$-$C_{12}$ aryloxy, with phenoxy preferred; and aralkyloxy, preferably $C_5$-$C_{12}$ aralkyloxy, with benzyloxy preferred. The alkoxy, aryloxy and aralkyloxy substituents are optionally heteroatom-containing and/or may be substituted with one or more, typically one or two substituents. Of course, it will be appreciated that any substituents should not be detrimental to the therapeutic efficacy of the compound, nor should they be reactive with or otherwise interact adversely with other components of the pharmaceutical composition in which the compound is contained.

Substituents include functional groups, hydrocarbyl groups, and combinations thereof as described in part (I) of this section.

In addition, either $R^1$ and $R^2$, or $R^2$ and $R^3$, can be linked to form a cyclic structure, which typically, although not necessarily, is selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents such as those enumerated above and zero to 3 heteroatoms. For example, either $R^1$ and $R^2$, or $R^2$ and $R^3$, can be joined to form a lower alkylene linkage, e.g., —$(CH_2)_3$— or —$(CH_2)_3$—, a lower alkylene linkage substituted with a substituent as described above, a lower heteroalkylene linkage, e.g., —O—$CH_2$—O—, —$CH_2$—O—$CH_2$, or —$CH_2$—NH—$CH_2$, in which case the remaining R group, i.e., $R^1$ or $R^3$, is hydroxyl, $C_1$-$C_6$ alkoxy, aryloxy, or aralkyloxy.

When α is present, $R^4$ is selected from O, S, $NR^x$, and $CR^yR^z$, and when α is absent, $R^4$ is selected from OH, SH, $NHR^x$, and $CR^yR^zH$, wherein $R^x$, $R^y$ and $R^z$ are hydrogen or alkyl. Preferably, $R^x$, $R^y$, and $R^z$ are hydrogen, such that $R^4$ is O, S, NH or $CH_2$ when α is present, and, when α is absent, $R^4$ is selected from OH, SH, $NH_2$ and $CH_3$. In a most preferred embodiment, $R^4$ is O when α is present, and, when α is absent, $R^4$ is OH.

When γ is present, then $R^5$ is O, S or $NR^x$, where $R^x$ is as defined above. Preferably, $R^x$ is hydrogen, and more preferably, $R^5$ is O. When γ is absent, $R^5$ is selected from the group consisting of OH, SH, $N(R^x)_2$ wherein the $R^x$ may be the same or different and are selected from hydrogen, alkyl, aryl, and aralkyl, and esters of the structure —O—(CO)—R (i.e., acyloxy groups) in which R is substituted or unsubstituted alkyl, aryl, or aralkyl. In preferred such esters, R is alkyl, particularly $C_1$-$C_6$ alkyl, or substituted phenyl. Generally, such acyloxy substituents have 2 to 32 carbon atoms, preferably 6 to 32 carbon atoms. A preferred acyloxy substituent has the structure

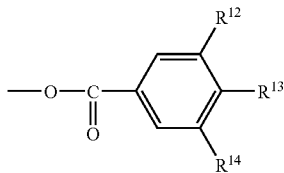

wherein $R^{12}$, $R^{13}$ and $R^{14}$ are independently selected from the group consisting of hydrogen, hydroxyl, alkoxy, aryloxy, and aralkyloxy. Within this group, the most preferred substituents are wherein $R^{12}$, $R^{13}$ and $R^{14}$ are independently selected from the group consisting of hydroxyl, $C_1$-$C_6$ alkoxy (preferably methoxy), and $C_5$-$C_{12}$ aralkyloxy (preferably benzyloxy).

$R^6$, $R^7$, $R^8$ and $R^9$ are independently selected from the group consisting of hydrogen, such that the phenyl ring is unsubstituted, and nonhydrogen ring substituents, the latter including hydrocarbyl, substituted hydrocarbyl, heteroatom-containing hydrocarbyl, substituted heteroatom-containing hydrocarbyl, and functional groups. Generally, $R^6$, $R^7$, $R^8$ and $R^9$ are independently selected from the group consisting of: hydrogen; alkyl, preferably $C_1$-$C_6$ alkyl, such as methyl and ethyl; alkenyl, preferably $C_2$-$C_6$ alkenyl, such as vinyl and allyl; aryl, including heteroaryl and substituted aryl, preferably $C_5$-$C_{12}$ aryl such as phenyl and substituted phenyl; aralkyl, preferably $C_6$-$C_{12}$ aralkyl, such as benzyl; alkoxy, preferably $C_1$-$C_6$ alkoxy, such as methoxy and ethoxy, with methoxy preferred; aryloxy, preferably $C_5$-$C_{12}$ aryloxy, with phenoxy preferred; and aralkyloxy, preferably $C_6$-$C_{12}$ aralkyloxy, with benzyloxy preferred. In addition, (a) $R^6$ and $R^7$, (b) $R^7$ and $R^8$, or (c) $R^8$ and $R^9$ may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms. In preferred such compounds, $R^6$ and $R^7$, or $R^8$ and $R^9$, are linked to form a phenyl or heteroaromatic ring (e.g., pyridinyl, pyrimidinyl, etc.) "fused" to the first. In other preferred compounds of this type, $R^7$ and $R^8$ are linked to form an alicyclic (e.g., a cyclohexyl) or heteroalicyclic ring fused to the phenyl ring indicated in the structure. The ring formed by linkage of $R^6$ to $R^7$, or of $R^7$ to $R^8$, or of $R^8$ to $R^9$, may be further substituted in a similar manner to form a fused tricyclic structure such as an anthracene, phenanthrene, or benzo[h]quinoline system. Particularly preferred such compounds are α-naphthaflavanoids, wherein $R^6$ and $R^7$ are hydrogen, and $R^8$ and $R^9$ are linked to form a phenyl ring, and 1,2,3,4-tetrahydro-β-naphthaflavanoids, wherein $R^6$ and $R^9$ are hydrogen, and $R^7$ and $R^8$ are linked to form a cyclohexyl ring.

$R^{10}$ and $R^{11}$ are independently selected from the group consisting of hydrogen, hydroxyl, $C_1$-$C_6$ alkyl, $C_1$-$C_6$ alkoxy, and halo. Preferably, $R^{10}$ and $R^{11}$ are hydrogen.

One type of compound encompassed by structural formula (I) is a flavanone, wherein α and γ of formula (I) are present, β is absent, $R^4$ is O, and $R^5$ is O. Such compounds have the structure of formula (II)

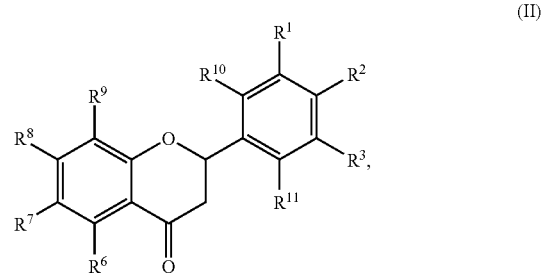

wherein $R^1$ through $R^3$ and $R^6$ through $R^{11}$ are as defined above for formula (I).

Another type of compound encompassed by structural formula (I) is a flavanol, in which α of formula (I) is present, β and γ are absent, $R^4$ is OH, and $R^5$ is OH. These flavanols have the structure of formula (III)

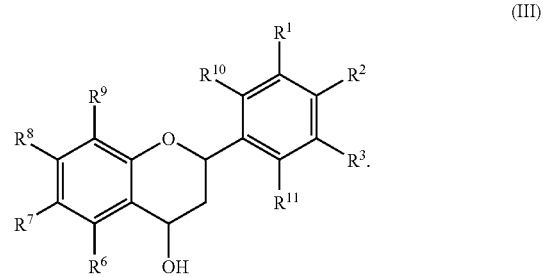

As above, $R^1$ through $R^3$ and $R^6$ through $R^{11}$ are as defined above for formula (I). These flavanols may be prepared from the flavanones of formula (II) using a simple reduction reaction. With compounds of formula (III), it will be appreciated that because of the two chiral centers, four different enantiomers are possible, and the compound may be in the form of an individual enantiomer or as a racemic mixture of enantiomers. In the following representation, the chiral centers are represented with a * and the bonds with alternative configurations are indicated by ∿:

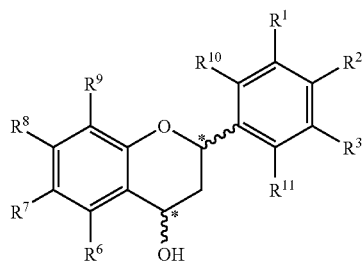

Accordingly, the four possible enantiomers are as follows:

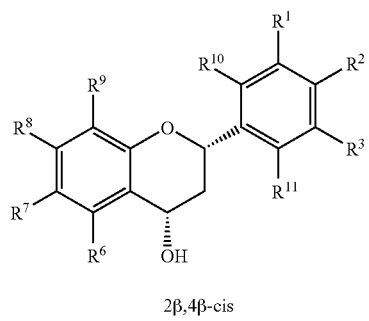

2β,4β-cis (IIIA)

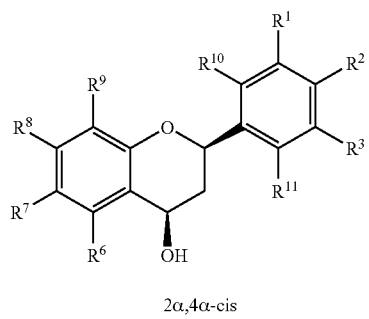

2α,4α-cis (IIIB)

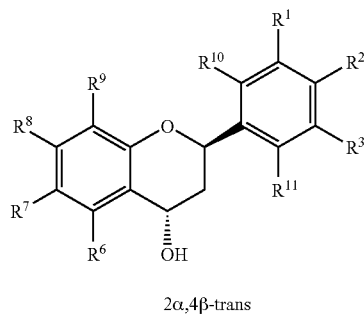

2α,4β-trans (IIIC)

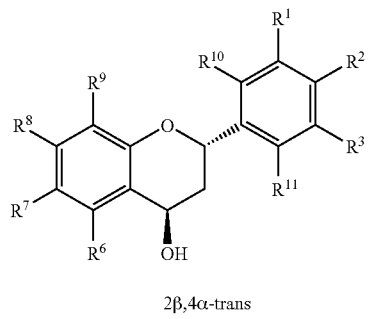

2β,4α-trans (IIID)

Generally, although not necessarily, the flavanol compound of the invention will be a racemic mixture of the two trans enantiomers. Such a mixture is indicated in the molecular structures herein as follows:

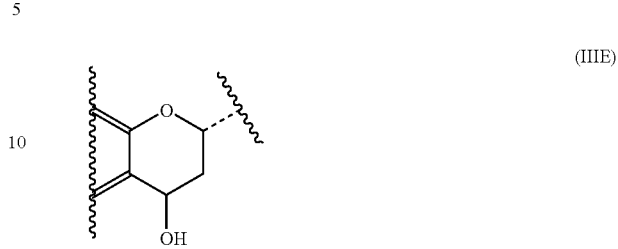

(IIIE)

Flavanol compounds in the form of a racemic mixture of the two cis enantiomers are represented by the following structure:

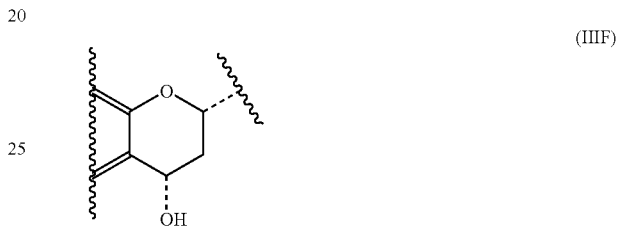

(IIIF)

Another type of compound encompassed by structural formula (I) is a chalcone, in which β and γ of formula (I) are present, α is absent, $R^4$ is OH, and $R^5$ is O, such that the compounds have the structure of formula (IV)

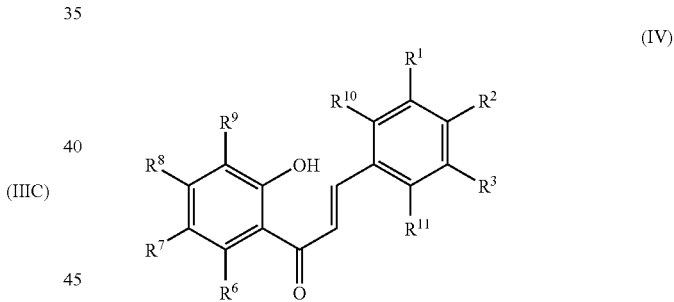

(IV)

wherein $R^1$ through $R^3$ and $R^6$ through $R^{11}$ are as defined above.

Preferred compounds of formula (I) are those wherein:
$R^1$, $R^2$ and $R^3$ are identical, and are selected from the group consisting of $C_1$-$C_6$ alkoxy and benzyloxy;
when α is present, $R^4$ is O, and when α is absent, $R^4$ is OH;
when γ is absent, then $R^5$ is selected from the group consisting of hydroxyl and acyloxy substituents having the structure

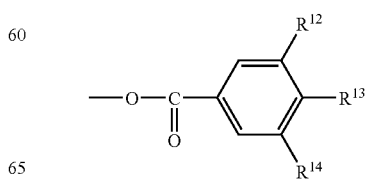

in which $R^{12}$, $R^{13}$ and $R^{14}$ are independently selected from the group consisting of hydrogen, hydroxyl, $C_1$-$C_6$ alkoxy, and benzyloxy;

(a) $R^6$ and $R^7$ are linked together to form a cyclohexyl, cyclopentyl, or phenyl ring, and $R^8$ and $R^9$ are hydrogen or $C_1$-$C_6$ alkoxy, (b) $R^8$ and $R^9$ are linked together to form a cyclohexyl, cyclopentyl, or phenyl ring, and $R^6$ and $R^7$ are hydrogen or $C_1$-$C_6$ alkoxy, (c) $R^7$ and $R^8$ are linked to form a cyclohexyl, cyclopentyl, or phenyl ring, and $R^6$ and $R^9$ are hydrogen, or (d) $R^6$ and $R^8$ are $C_1$-$C_6$ alkoxy or benzyloxy and $R^7$ and $R^9$ are hydrogen; and $R^{10}$ and $R^{11}$ are hydrogen.

Particularly preferred compounds of formula (I) are wherein:

$R^1$, $R^2$ and $R^3$ are identical, and are selected from the group consisting of methoxy and benzyloxy;

when α is present, $R^4$ is O, and when α is absent, $R^4$ is OH;

when γ is absent, $R^5$ is OH;

when γ is present, $R^5$ is O;

$R^6$ and $R^7$ are hydrogen;

$R^8$ and $R^9$ are linked together to form a phenyl ring;

$R^{10}$ and $R^{11}$ are hydrogen; and $R^{12}$, $R^{13}$ and $R^{14}$ are independently selected from the group consisting of hydroxyl, methoxy and benzyloxy.

Accordingly, particularly preferred flavanols of the invention have the structure (V)

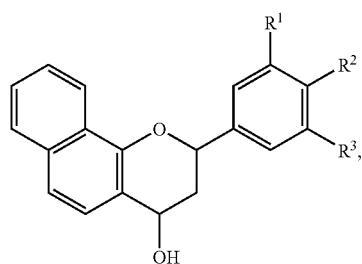

(V)

optimally having the trans structure (VI)

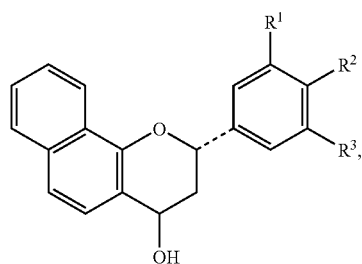

(VI)

wherein, in a most preferred embodiment, $R^1$, $R^2$, and $R^3$ are methoxy or benzyloxy.

Particularly preferred flavanones of the invention have the structure (VIII)

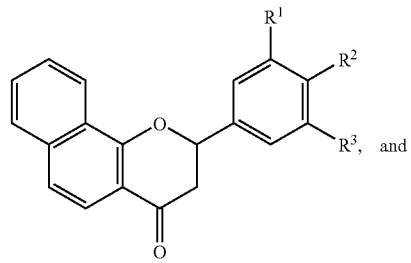

(VIII)

particularly preferred chalcones have the structure of formula (IX)

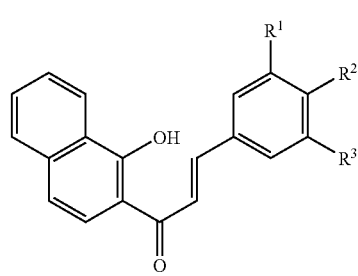

(IX)

wherein, again, in a most preferred embodiment, $R^1$, $R^2$, and $R^3$ are methoxy or benzyloxy.

Specific examples of compounds of the invention include, but are not limited to, the following.

SR 13176:

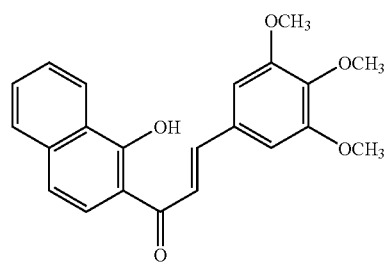

SR 13177:

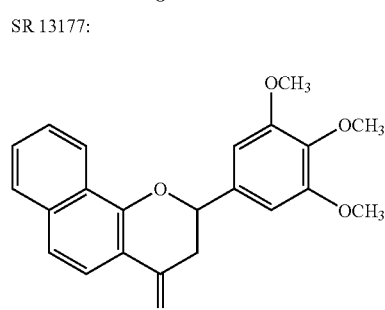

-continued
SR 13178:
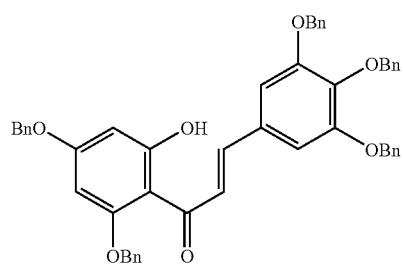
SR 13179:
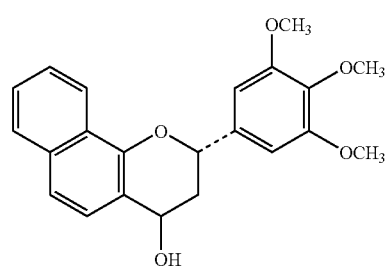
SR 13180:
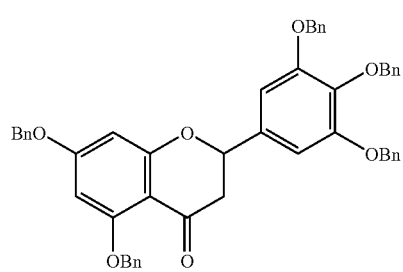
SR 13181:
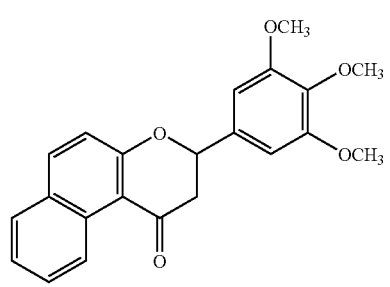
SR 13182:
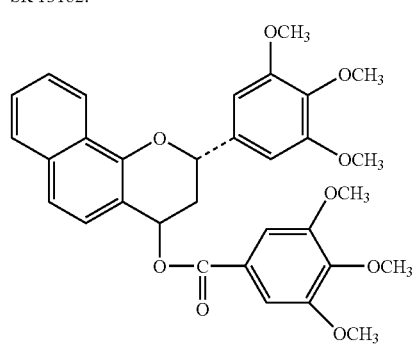
-continued
SR 13183:
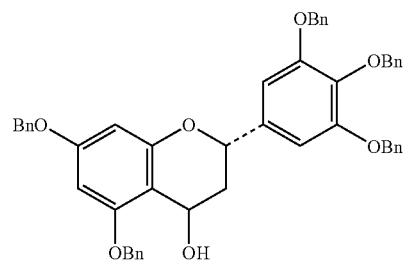
SR 13185:
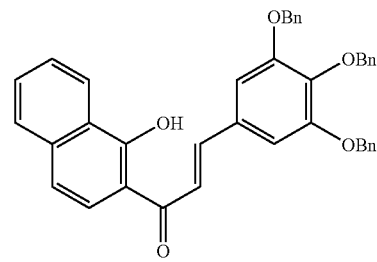
SR 13186:
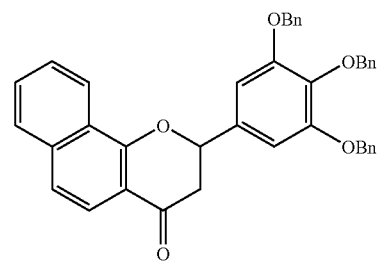
SR 13187:
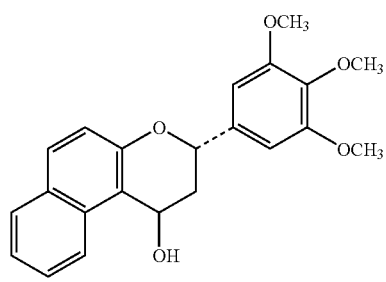
SR 13188:
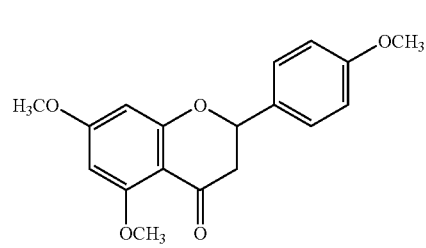

-continued
SR 13189:
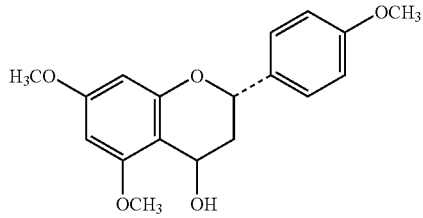
SR 13191:
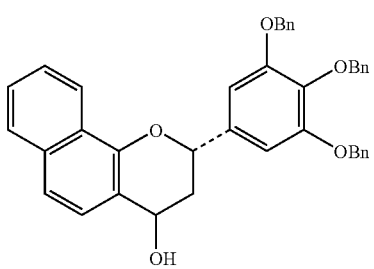
SR 13801:
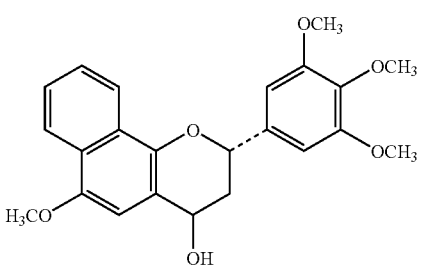
SR 13802:
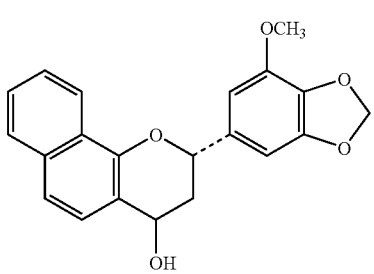
SR 13803:
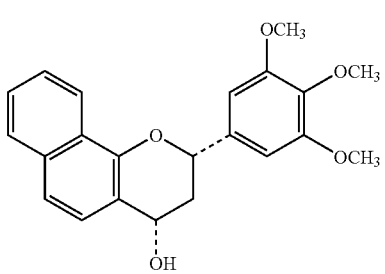
-continued
SR 13804:
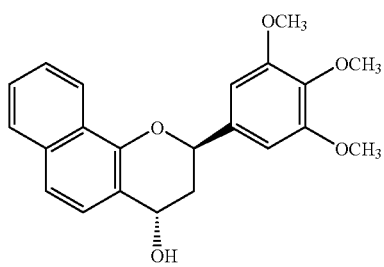
SR 13805:
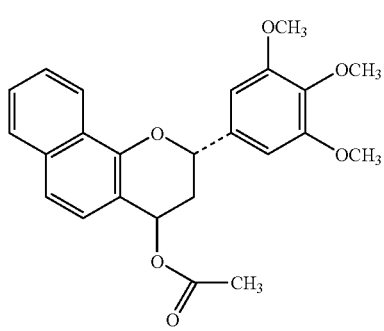
SR 13806:
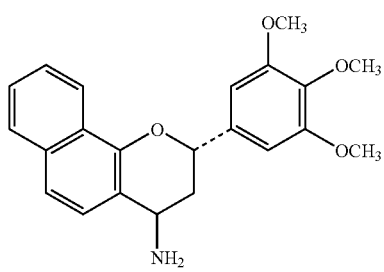
SR 13807:
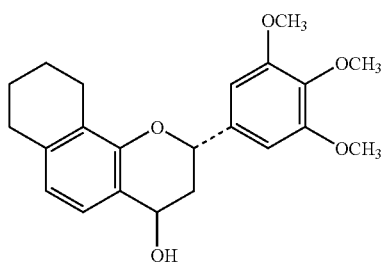
SR 13808:
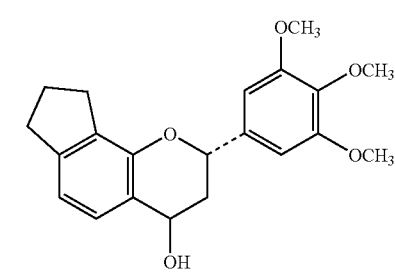

SR 13809:

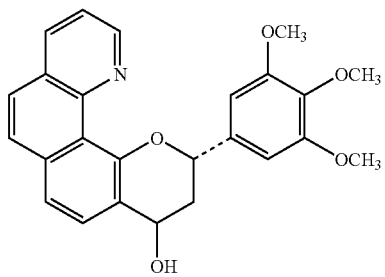

SR 13810:

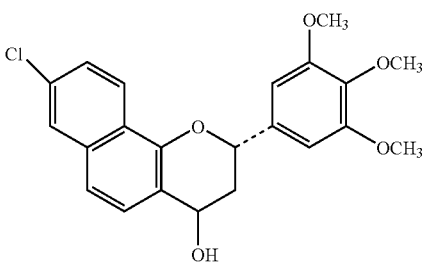

SR 13811:

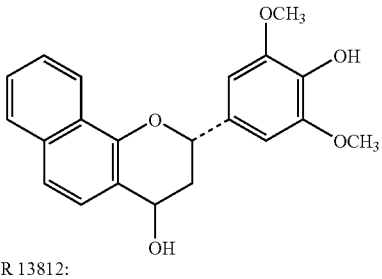

SR 13812:

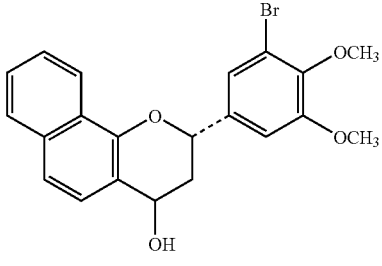

SR 13817:

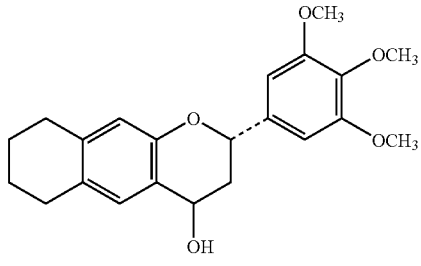

A compound of the invention may be administered in the form of a salt, ester, amide, prodrug, active metabolite, analog, or the like, provided that the salt, ester, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992).

For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

In addition, those novel compounds containing chiral centers can be in the form of a single enantiomer or as a racemic mixture of enantiomers. In some cases, i.e., with regard to certain specific compounds illustrated herein, chirality (i.e., relative stereochemistry) is indicated. In other cases, it is not, and such structures are intended to encompass both the enantiomerically pure form of the compound shown as well as a racemic mixture of enantiomers. Preparation of compounds in enantiomerically pure form may be carried out using an enantioselective synthesis; alternatively, the enantiomers of a chiral compound obtained in the form of the racemate may be separated post-synthesis, using routine methodology.

Other derivatives and analogs of the active agents may be prepared using standard techniques known to those skilled in the art of synthetic organic chemistry, or may be deduced by reference to the pertinent literature.

The compounds of the invention may be readily synthesized using straightforward techniques. For example, compounds of formula (II) can be prepared by condensing the ketone (X) with the aromatic aldehyde (XI) in the presence of a nitrogenous organic base, e.g., in an amine solvent such as a mixture of pyridine and piperidine, according to the following scheme:

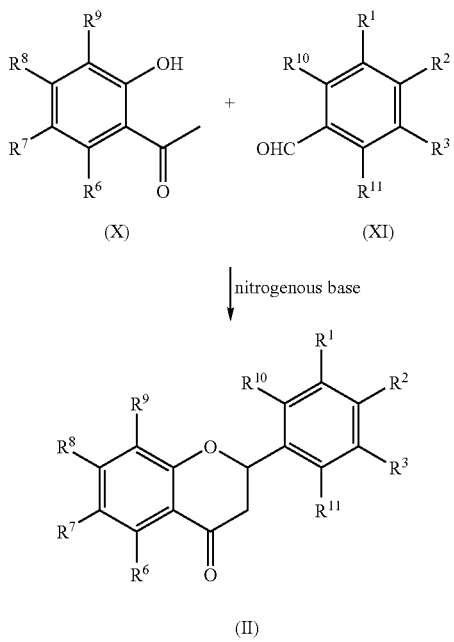

(X)    (XI)

↓ nitrogenous base (II)

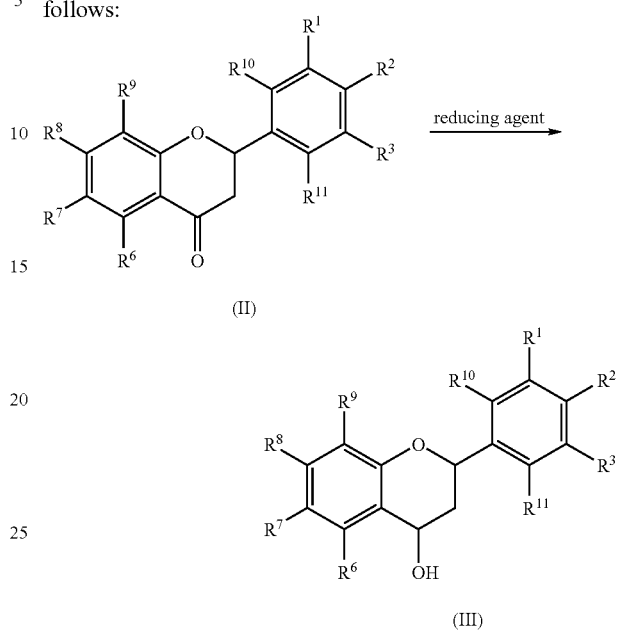

(II)

→ reducing agent (III)

Preferably, the reaction is carried out at reflux. Specific such reactions are described in Examples 2, 5, 7, 10, and 12.

To synthesize the chalcone (IV), ketone (X) and aromatic aldehyde (XI) are used as starting materials, as above, but in this case the reaction is carried out in the presence of an aqueous inorganic base, preferably a strong base (e.g., potassium hydroxide or sodium hydroxide), followed by acidification:

Flavanols, having the structure of formula (III), may be readily derived from formula (II) compounds using a straightforward reduction reaction, e.g., treatment of the flavanone (II) with a reducing agent such as sodium borohydride, as follows:

In most cases, the reduction is enantioselective with respect to preparation of a racemic mixture of the 2α, 4βtrans and 2β, 4α-cis enantiomers providing the product in at least a 60-80% yield. Specific such reactions are described in Examples 3, 6, 8, 11, 13, and 14.

Compounds of formula (I) wherein γ is not present and $R^5$ is acyloxy can be prepared as described in Example 9, by reaction of a flavanol of formula (III) with an acyl halide to convert the 4-hydroxy group to the desired 4-acyloxy group, according to the following scheme:

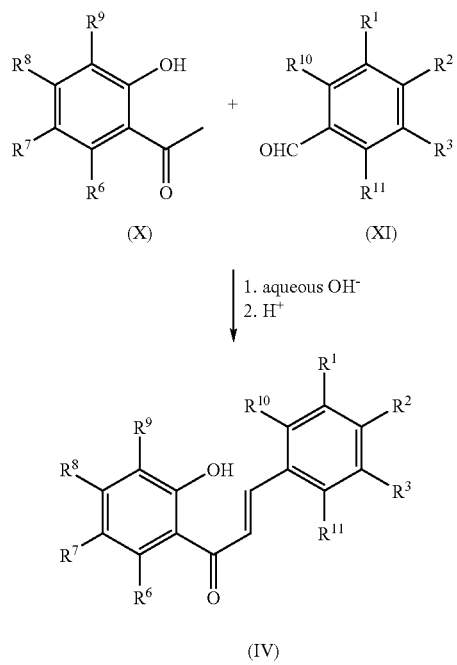

(X)    (XI)

↓ 1. aqueous OH⁻
   2. H⁺

(IV)

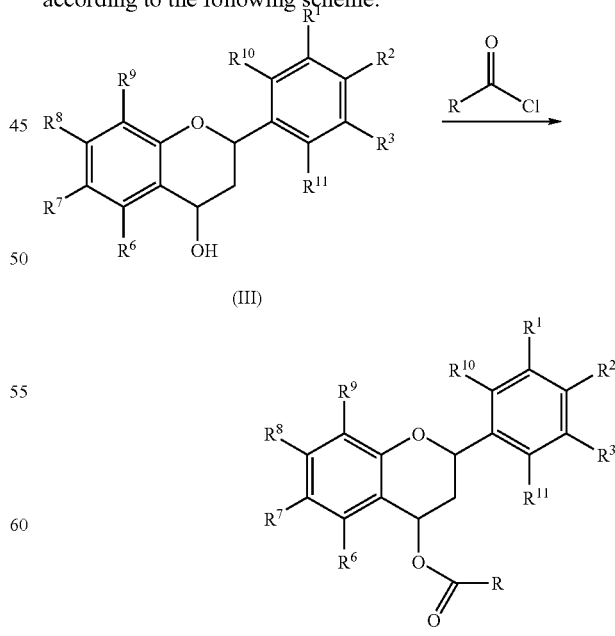

(III)

(XII)

This reaction may be carried out at ambient temperature. Specific such reactions are described in Examples 1, 4, and 10.

In the scheme, R is substituted or unsubstituted alkyl, aryl, or aralkyl, preferably a substituted phenyl group having the structure

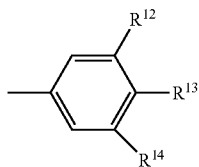

wherein $R^{12}$, $R^{13}$ and $R^{14}$ are independently selected from the group consisting of hydrogen, hydroxyl, alkoxy, aryloxy, and aralkyloxy. If the flavanol reactant (III) is in the form of a pure enantiomer, the stereochemistry will be maintained during acylation, such that the product (XII) has the same configuration as the starting material. For example, acylation of (IIIA) will result in an acylated product having the structure (XIIA), as follows:

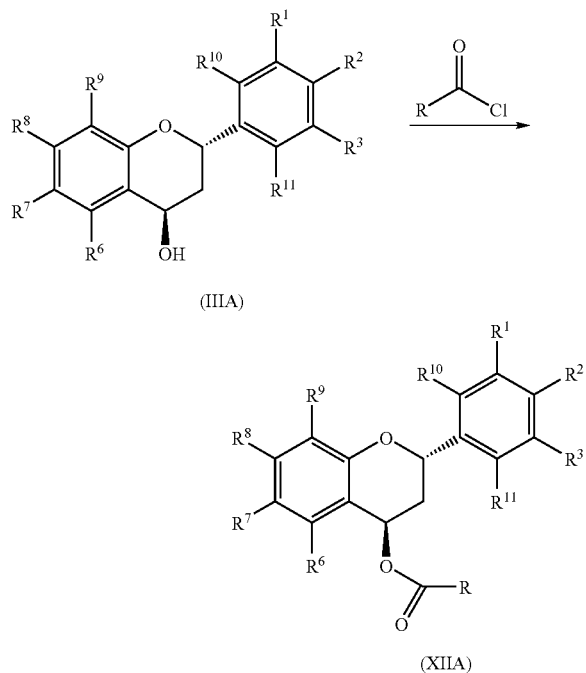

III. Pharmaceutical Formulations and Modes of Administration

The novel flavanoids may be conveniently formulated into pharmaceutical formulations composed of one or more of the compounds in association with a pharmaceutically acceptable carrier. See *Remington: The Science and Practice of Pharmacy*, 19th Ed. (Easton, Pa.: Mack Publishing Co., 1995), which discloses typical carriers and conventional methods of preparing pharmaceutical formulations.

The compounds of the invention may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subject's weight, the mode of administration and other pertinent factors known to the prescribing physician. Generally, however, dosage will be in the range of approximately 0.001 mg/kg/day to 100 mg/kg/day, more preferably in the range of about 0.1 mg/kg/day to 10 mg/kg/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy*, 19th Ed. (Easton, Pa.: Mack Publishing Co., 1995).

As the present compounds are orally active, oral dosage forms are generally preferred, and include tablets, capsules, caplets, and nonaqueous solutions, suspensions and or syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, Nineteenth Edition. (1995) cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compositions will generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol. Transdermal administration is also a suitable delivery route for compounds of the invention.

IV. Utility

The compounds of the invention can be used to treat a variety of disorders, and are primarily useful in treating cancer and other hyperproliferative diseases, particularly diseases characterized by or dependent upon hyperproliferation of blood vessels (pathologic angiogenesis). The compounds are useful in the treatment of both primary and metastatic solid tumors and carcinomas of, without limitation, the breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, germ cells, and ovaries; embryo and fetus; male genital tract including prostate, seminal vesicles, testes, and germ cells; endocrine glands including thyroid, adrenal, and pituitary; skin (including hemangiomas, melanomas, sarcomas arising from bone or soft tissues and Kaposi's sarcoma); and the brain, nerves, eyes, and meninges (including astrocytomas, gliomas, glioblastomas, retinoblastomas, neuromas, neuroblastomas, Schwannomas, and meningiomas). The compounds are also useful in treating solid tumors arising from hematopoietic malignancies such as leukemias, including chloromas, plasmacytomas, plaques and tumors of mycosis fungoides, and cutaneous T-cell lymphoma/leukemia; and lymphomas, including both Hodgkin's and non-Hodgkin's lymphomas. The compounds are of particular use in treating cancers of the breast, ovary, prostate, liver, lung, and pancreas, including drug-resistant forms of these cancers. Efficacy against drug-resistant cancers represents an important advance in the art, as a major problem affecting the efficacy of chemotherapy regimens is the evolution of cancer cells that, upon exposure to a chemotherapeutic drug, become resistant to a multitude of structurally unrelated drugs and therapeutic agents.

The compounds of the invention are also useful in the treatment and prevention of angiogenesis-associated diseases other than cancer. Such diseases include rheumatoid, immune, and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia, and other abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids); and diseases that have angiogenesis as a pathologic consequence, including cat scratch disease and ulcers (*Helicobacter pylori* infection). Another use is as a birth control agent that inhibits ovulation and establishment of the placenta. It will be appreciated by those skilled in the art that numerous other uses of the present compounds are possible as well.

In one embodiment, the compounds of the invention are also useful in the inhibition of tumor cell invasion through an extracellular matrix. Typically, matrix metalloproteinases (MMPs) are involved in breaking down the extracellular matrix, thereby facilitating cellular invasion. The various MMPs include, without limitation, MMP-2, MMP-9, membrane-type 1 MMP (MT1-MMP), and matrilysin-2 (MMP-26), and are regulated by one or more inhibitors of metalloproteinases, including the tissue inhibitor of metalloproteinase 1 (TIMP-1), TIMP-2, and TIMP-3.

TIMP-2 controls matrix proteolysis by modulating the interaction between membrane-type 1 MMP (MT1-MMP) and proMMP-2 that is required for the formation of active MMP-2. TIMP-2 also inhibits cell growth by suppressing tyrosine kinase-type receptor growth factor signaling. Furthermore, TIMP-2 up-regulates mitogen-activated protein kinase phosphatase 1 in an MMP-independent manner. Upregulation of mitogen-activated protein kinase phosphatase 1 results in dephosphorylation of p38 mitogen-activated protein kinase (p38 MAPK) leading to inhibition of tumor growth and angiogenesis. In addition, inhibition of p38 MAPK in oral squamous cell carcinoma and SSC25 results in enhanced TIMP-2 expression and decreased ECM degradation.

In one embodiment, the compounds of the invention are capable of stimulating the endogenous production of one or more of these metalloproteinase inhibitors. Induction of TIMP-1, TIMP-2, and/or TIMP-3 results in increased inhibition of extracellular matrix breakdown; tumor cell migration is thereby limited or eliminated. In this way, the compounds of the invention which stimulate the production of such metalloproteinase inhibitors are expected to be useful in treating diseases characterized by cellular migration, including for example cancer.

In another embodiment, the compounds of the invention are also useful in treating diseases characterized by growth and/or migration of endothelial cells. Without wishing to be bound by theory, it is believed that the compounds useful in this sense are capable of inhibiting endothelial cell proliferation and/or migration via interactions with cell surface receptors on endothelial cells. TIMP-2, for example, inhibits endothelial cell proliferation and function through non-MMP-dependent mechanisms, via interactions with cell surface receptors on endothelial cells. The compounds of the invention are able to inhibit endothelial cell proliferation, for example, by stimulating TIMP-2 production. Thus, for example, because angiogenesis requires endothelial cell proliferation and migration, the compounds of the invention that are useful in inhibiting endothelial cell proliferation and/or migration may therefore be useful as antiangiogenic agents as described above.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

V. Experimental

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

1-Hydroxy-2-acetonaphthone, 3,4,5-trimethoxybenzaldehyde, 2-hydroxy-1-acetonaphthone, naringenin, and 4-methoxy-1-naphthol were purchased from Aldrich Chemical Co. All other reagents were used as also obtained from commercial suppliers unless otherwise indicated.

$^1$H and $^{13}$C NMR spectra were recorded on a Varian Gemini 300 MHz spectrometer (300 MHz and 75 MHz, respectively) and are internally referenced to chloroform at δ 7.27. Data for $^1$H NMR are reported as follows: chemical shift (δ ppm), multiplicity (s=singlet, d=doublet, t=triplet, q=quartet, m=multiplet), coupling constant (Hz), integration, and assignment. Data for $^{13}$C are reported in terms of chemical shift. IR spectra were recorded on a Perkin-Elmer 1610 spectrometer and are reported in terms of frequency of absorption (cm$^{-1}$). Mass spectra were obtained using a ThermoFinnigan LCQ Duo LC/MS/MS instrument and an electrospray ionization probe. Thin-layer chromatography was run on Analtech Uniplate silica gel TLC plates.

Western Blotting. Proteins were separated by gel electrophoresis using 4-12% pre-cast SDS-polyacrylamide gels (Invitrogen, Carlsbad, Calif.) and then electrophoretically transferred onto Hybond™-P membrane (Amersham Biosciences, Piscataway, N.J.). Blots were probed with specific antibodies (Santa Cruz Biotechnology, Inc). The ECL Plus Western Blotting Detection System of Amersham Biosciences (Piscataway, N.J.) and the procedure recommended by the manufacturer was used for the detection of antigens. Protein bands were quantified by analyzing the images obtained using an Alphaimager™ S-3400 (Alpha Innotech Corp., San Leandro, Calif.).

Zymography. Zymography as used herein is illustrated by the following general procedure. MCF10CA1a cells were grown in 100 mm in diameter tissue culture plates until 90% confluent. The cells were washed once with serum-free medium and placed in serum-free medium for 2 h prior to drug treatment. The candidate agent was added to the plate and the plate was incubated in the 5% $CO_2$ incubator at 37° C. for 16 h. The medium was collected, concentrated and subjected to zymography. In brief, 10 μl of the sample was electrophoresed in 8% polyacrylamide gel containing 0.1% gelatin in the presence of SDS. After electrophoresis, gel was washed two times, 20 min each, in 2.5% Triton X-100 and incubated overnight at 37° C. in a solution containing 50 mM Tris-HCl, pH 8, 5 mM $CaCl_2$, 10 mM $ZnCl_2$ and 0.02% $NaN_3$. The gel was then stained for 30 min with 0.5% Coomassie Brilliant Blue R-250 prepared in 30% methanol/10% acetic acid solution and destained with several washes with water.

Northern blotting. Ten μg of total RNA was electrophoresed in 1% agarose gel containing 6% formaldehyde, transferred to nylon membrane (Amersham Hybond N) by capillary blotting and fixed to the filter by exposure to UV. The blot was probed with a 600 bp $^{32}$P-labeled cDNA sequence of human TIMP-2. Hybridizations were carried out at 42° C. in 50% formamide, 5×SSC, 5×Denhardt's solution, 0.1% SDS, and 0.3 mg/ml salmon sperm DNA. Filters were exposed to X-ray film (Kodak XAR-2) at −80° C. using an intensifying screen (Coronex Hi-Plus).

In these examples and throughout this patent, unless otherwise stated, the abbreviations employed have their generally accepted meanings, as follows:
Bn=benzyl
CAM=chick chorioallantoic membrane
$CH_2Cl_2$=methylene chloride
DBU=1,3-diazabicyclo[5.4.0]undec-7-ene
DMAP=dimethylamino pyridine
DMF=dimethyl formamide
EGM=endothelial cell growth medium eq.=equivalent(s)
EtOAc=ethyl acetate
EtOH=ethanol
g=gram
HUVEC: human umbilical vein endothelial cells
KOH=potassium hydroxide
Me=methyl
mL=milliliter
MTT=3-(4,5-dimethylthiazol-2-yl)-2,5-diphenyl tetrazolium bromide
MVD=microvessel density
PCNA=proliferating cell nuclear antigen
Ph=phenyl
THF=tetrahydrofuran
TLC=thin layer chromatography

EXAMPLE 1

SYNTHESIS OF 1-(1-HYDROXY-NAPHTHALEN-2-YL)-3-(3,4,5-TRIMETHOXYPHENYL)-PROPENONE (SR 13176)

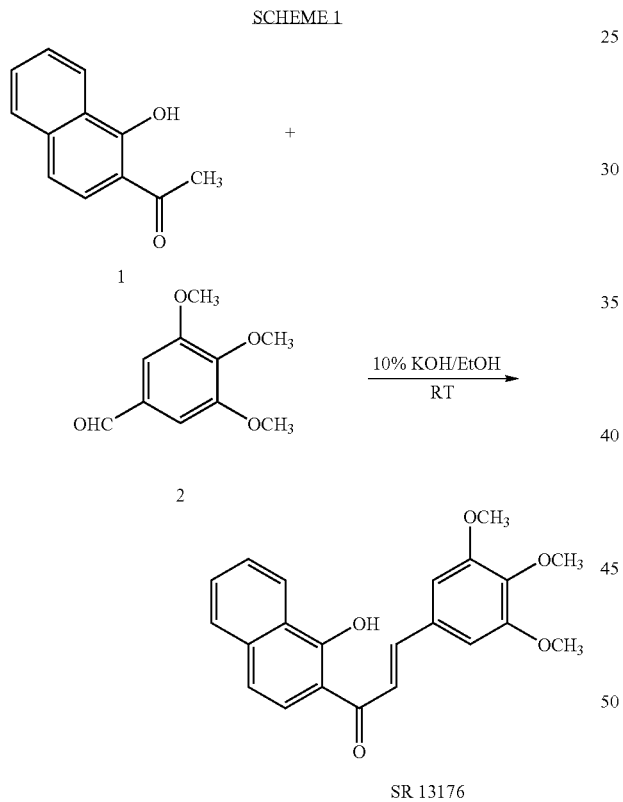

1-(1-Hydroxy-naphthalen-2-yl)-3-(3,4,5-trimethoxyphenyl)-propenone (SR 13176) was synthesized according to Scheme 1 as follows: A mixture of 1-hydroxy-2-acetonaphthone 1 (10 g, 54 mmol) and 3,4,5-trimethoxy-benzaldehyde 2 (15.79 g, 80 mmol) in 200 mL of 10% KOH/EtOH, was stirred at room temperature for 48 h. The dark solution was then poured into 400 mL water and acidified to pH 4 with 6N hydrochloric acid. A sticky solid precipitated out and the supernatant was decanted off. The sticky residue was dissolved in boiling methanol (200 mL) and cooled overnight at 4° C. The reddish orange crystals formed were filtered off, washed with cold methanol, and dried in the drying pistol (under refluxing acetone) for 16 h, to afford 9.58 g (49%) pure SR 13176 as red crystalline solid. The supernatant containing unreacted acetonaphthone and the product was purified via flash column chromatography eluting with a gradient of hexanes and ethyl acetate (95:5 to 85:15) to obtain an additional 1.25 g of the chalcone SR 13176. Total yield: 55%. m.p. 115° C.; TLC: Hexanes: EtOAc (7:3): $R_f$=0.36; $^1$H NMR (300 MHz, CDCl$_3$): δ 4.05 (s, 3H, OCH$_3$), 4.06 (s, 6H, OCH$_3$), 7.04 (s, 2H, 2',6'-Ar—H), 7.31 (d, J=9.03 Hz, 1H, C$\underline{H}$=CH), 7.54-7.67 (m, 3H, Ar—H), 7.63-7.93 (m, 3H, CH=C$\underline{H}$, Ar—H), 8.50 (d, J=8.16 Hz, Ar—H), 14.93 (s, 1H, OH); $^{13}$C (75 MHz, CDCl$_3$): δ 56.38 (OCH$_3$), 61.04 (OCH$_3$), 106.20, 106.30, 113.51, 118.19, 119.73, 123.93, 124.56, 125.97, 127.41, 130.21, 130.29, 137.42, 145.26, 153.63, 164.45, 193.07. Anal. calcd. for $C_{22}H_{20}O_5$; C, 72.51; H, 5.53; Found: C, 72.39; H, 5.61.

Scheme 2 illustrates the syntheses of SR 13177 and SR 13179, as described in Examples 2 and 3, respectively:

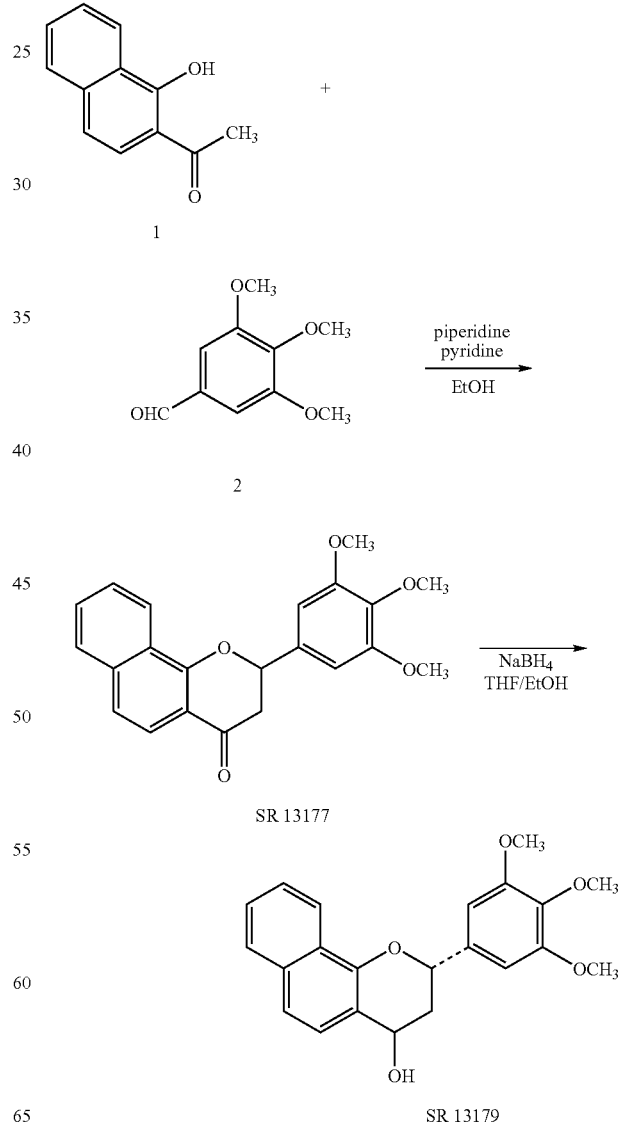

EXAMPLE 2

Synthesis of 2-(3,4,5-Trimethoxyphenyl)-2,3-dihydrobenzo[h]chromen-4-one (SR 13177)

A mixture of 1-hydroxy-2-acetonaphthone 1 (15 g, 81 mmol) and 3,4,5-trimethoxy-benzaldehyde 2 (17.66 g, 88 mmol) in 600 mL ethanol was treated with piperidine (40 mL) and pyridine (45 mL) and the dark solution was refluxed for 18 h. The reaction mixture was evaporated to dryness and the dark residue was dissolved in methylene chloride (600 mL). The solution was washed with 2×300 mL of water and 2×300 mL brine and dried with anhydrous $MgSO_4$ after which it was filtered and evaporated to afford 60 g of crude material. This was purified via flash chromatography, eluting with methylene chloride (1 L), followed by the solvent mixture $CH_2Cl_2$:EtOAc (95:5) to obtain fractions containing pure product. These were evaporated to afford 11.4 g (39% yield) of pure SR 13177 as a yellow solid. TLC: Hexanes/EtOAc (7:3): $R_f$=0.26; $^1$H NMR (300 MHz, $CDCl_3$): δ 3.00 (dd, J=16.69, 3.15, 1H, 3-H), 3.22 (dd, J=16.94, 13.28, 1H, 3-H), 3.92 and 3.94 (2s, 9H, $OCH_3$), 5.66 (dd, J=13.31, 3.17, 1H, 2-H), 6.81 (s, 2H, 2',6'-Ar—H), 7.46-7.95 (m, 5H, Ar—H), 8.36 (d, 1H, Ar—H); $^{13}$C (75 MHz, $CDCl_3$): δ 44.27 (C-3), 56.35 ($OCH_3$), 60.89 ($OCH_3$), 80.62 (C-2), 103.49, 115.61, 121.47, 123.61, 124.91, 126.34, 127.94, 129.71, 134.4, 137.67, 153.68, 159.71, 191.42. Anal. calcd. for $C_{22}H_{20}O_5$; C, 72.51; H, 5.53; Found: C, 72.35; H, 5.64.

EXAMPLE 3

Synthesis of 2-(3,4,5-Trimethoxyphenyl)-3,4-dihydro-2H-benzo[h]chromen-4-ol (SR 13179)

Sodium borohydride (0.55 mmol, 21.2 mg) was added to a solution of the flavanone SR 13177 (1.1 mmol, 0.4 g) in THF (5 mL) and 95% ethanol (10 mL). The reaction was warmed to a gentle reflux for 2.5 h. The cooled reaction mixture was evaporated to dryness and the residue was dissolved in ethyl acetate, and the organic solution was washed with water and brine and dried ($MgSO_4$). The crude product obtained by evaporation of the ethyl acetate solution, was purified by flash column chromatography and the pure product was eluted with hexanes/ethyl acetate (8:2). Fractions containing pure product were evaporated to give a light yellow, foamy crystalline solid, SR 13179 (0.325 g, 81% yield). TLC: Hexanes/EtOAc (1:1): $R_f$=0.31; $^1$H NMR (300 MHz, $CDCl_3$): δ 1.90 (s, 1H, OH), 2.23-2.35 (ddd, J=13.23, 9.90, 11.37 Hz, 1H, 3-H axial), 2.64-2.71 (ddd, J=13.25, 6.39, 2.67 Hz, 1H, 3-H equatorial), 3.90 (m, 9H, $OCH_3$), 5.27 (m, 1H, 4-H), 5.33 (dd, J=11.33, 1.95 Hz, 1H, 2-H), 6.79 (s, 2H, 2',6'-H), 7.50 (m, 3H, Ar—H), 7.62 (d, 1H, Ar—H), 7.82 (m, 1H, Ar—H), 8.25 (m, 1H, Ar—H); $^{13}$C (75 MHz, $CDCl_3$): δ 40.24, 56.28, 60.89, 65.87, 77.20, 103.37, 119.19, 120.59, 122.15, 124.31, 124.83, 125.61, 126.59, 127.53, 134.18, 136.34, 149.53, 153.54. Anal. calcd. for $C_{22}H_{22}O_5$·0.1 $H_2O$, C, 71.76; H, 6.08; Found: C, 71.68; H, 6.23.

Scheme 3 illustrates the syntheses of SR 13178, SR 13180, and SR 13183, as described in Examples 4, 5, and 6, respectively:

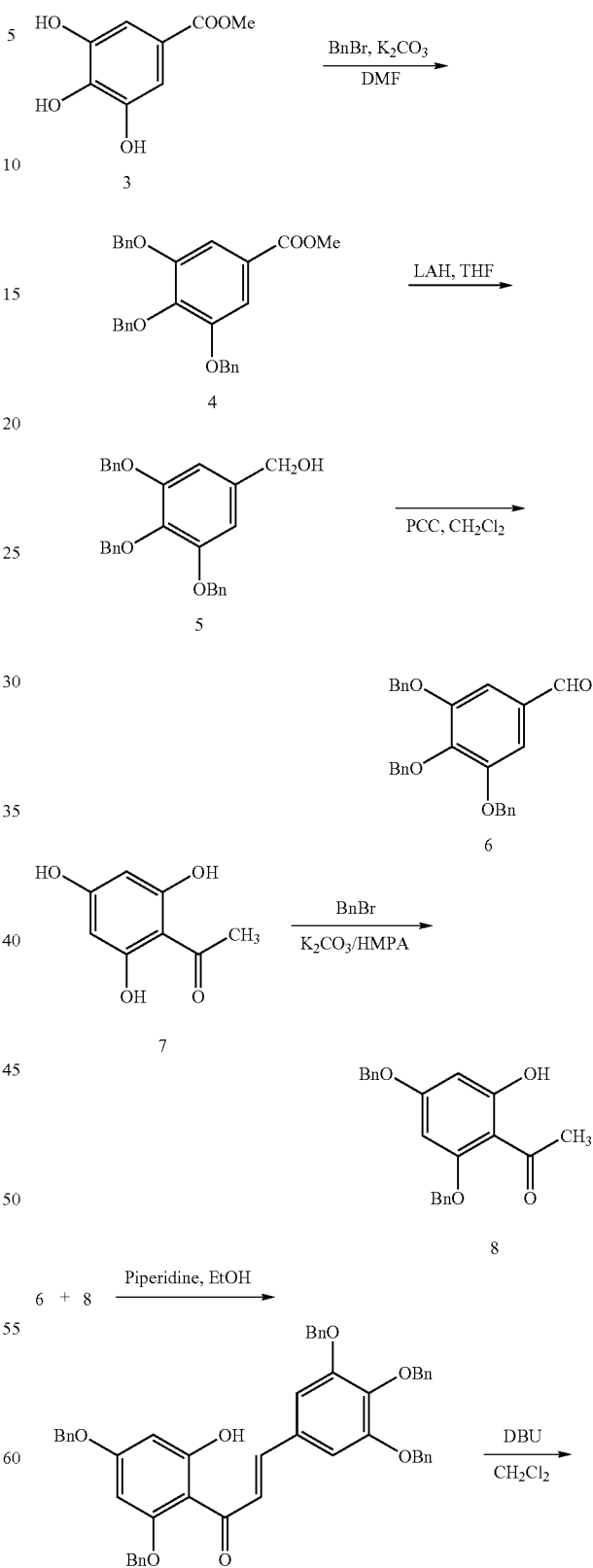

SCHEME 3

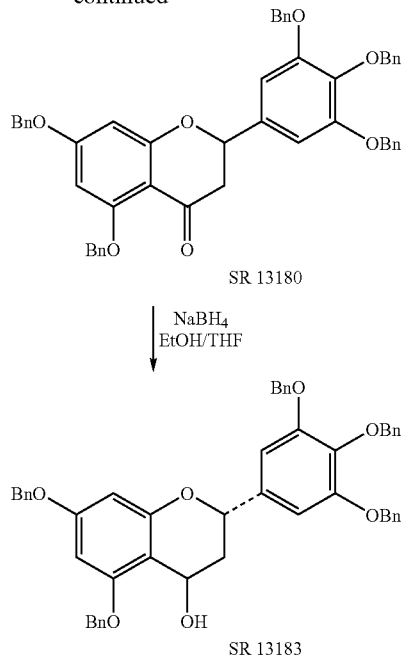

SR 13180

NaBH₄
EtOH/THF

SR 13183

EXAMPLE 4

SYNTHESIS OF 1-(2,4-BIS-BENZYLOXY-6-HYDROXY-PHENYL)-3-(3,4,5-TRIS-BENZYLOXY-PHENYL)-PROPENONE (SR 13178)

1-(2,4-Bis-benzyloxy-6-hydroxyphenyl)-3-(3,4,5-tris-benzyloxy-phenyl)-propenone (SR 13178) was synthesized according to Scheme 3, as follows:

(a) Preparation of 3,4,5-tribenzyloxybenzaldehyde 6 from methyl gallate 3:

A mixture of methyl gallate 3 (10 g, 53 mmol) and potassium carbonate (45 g, 320 mmol) in DMF (120 mL) was treated with benzyl bromide (210 mmol, 25.7 mL) and stirred at 40° C. under an argon atmosphere for 24 h. The reaction mixture was filtered and the filtrate evaporated to dryness. The residue was dissolved in minimum amount of methylene chloride and diluted with an equal volume of hexanes and loaded onto a short silica gel pad in a sintered glass funnel. The silica was eluted with hexanes (300 mL) to remove excess benzyl bromide and the eluant discarded. The product was then eluted with $CH_2Cl_2$: Hexanes (1:1, 300 mL) followed by methylene chloride (500 mL) and the eluants combined and evaporated to afford pure benzyl product 4 as an off-white solid (100% yield). $^1$H NMR (300 MHz, CDCl₃): δ 3.88 (s, 3H, CH₃), 5.11 and 5.13 (2s, 6H, OCH₂), 7.35-7.41 (m, 17H, Ar—H).

To a solution of 3,4,5-tribenzyl-methyl gallate 4 (10 g, 22 mmol) in dry THF (75 mL) was added solid lithium aluminum hydride (1.25 g, 33 mmol) in small portions. The suspension was heated to reflux under argon for 2 h. The reaction was cooled to 0° C. and carefully quenched with the dropwise addition of water. The slurry was then extracted with $CH_2Cl_2$. The organic solution was dried with saturated brine, followed by anhydrous magnesium sulfate, filtered and evaporated to afford the pure product 5 as a white solid (8.9 g, 95% yield).

$^1$H NMR (300 MHz, CDCl₃): δ 4.6 (d, 2H, CH₂), 5.04 and 5.11 (2s, 6H, OCH₂), 6.67 (s, 2H, 2,6-Ar—H), 7.25-7.43 (m, 15H, Ar—H).

To a solution of 3,4,5-tribenzyloxy-benzyl alcohol 5 (8.9 g, 21 mmol) in methylene chloride (200 mL) at 0° C. was added pyridinium chlorochromate (5.43 g, 25 mmol) in small portions with vigorous stirring. The cooling was discontinued and reaction stirred at room temperature for 4 h. The dark brown suspension was filtered over a long pad of silica gel in a sintered glass funnel, and eluted with $CH_2Cl_2$, until all the pure product eluted out. The organic filtrate was evaporated down to give the pure product 6 as a soft white solid (8.1 g, 91.5% yield). $^1$H NMR (300 MHz, CDCl₃): δ 5.16 (s, 6H, OCH₂), 7.18 (s, 2H, 2,6-Ar—H), 7.26-7.41 (m, 15H, Ar—H), 9.80 (s, 1H, CHO).

(b) Preparation of 4',6'-bisbenzyloxy-2'-hydroxyacetophenone (8) from 2',4',6'-trihydroxyacetophenone 7:

A mixture of 2',4',6'-trihydroxyacetophenone (20 g, 0.12 mol, dried in the oven at 140° C.) and anhydrous potassium carbonate (50 g, 0.36 mol) in hexamethylphosphoramide (160 mL) was treated with benzyl chloride (30 mL, 0.26 mol), and the suspension heated at 90-93° C., under an argon atmosphere, for 1.5 h. The mixture was then cooled and filtered. The filtrate was added to 300 mL ice-cold water and acidified to pH 4 with 6N hydrochloric acid. The resulting suspension was heated to 70° C. for 1 h, and then cooled at 4° C. for 16 h. The deposited sticky solid was filtered off and washed with water. This solid was air-dried, and recrystallized from boiling methanol/acetone (2:1). Cooling the solution afforded the product 8 as off-white crystals (27.55 g, 66.5% yield). $^1$H NMR (300 MHz, CDCl₃): δ 2.56 (s, 3H, CH₃), 5.06 (s, 4H, CH₂), 6.10 and 6.16 (2s, 2H, 3',5'-Ar—H), 7.40 (m, 10H, Ar—H), 14.01 (s, 1H, OH).

(c) Preparation of SR 13178 from (6) and (8):

A mixture of 3,4,5-tribenzyloxybenzaldehyde 6 (2.66 g, 6.3 mmol) and 4',6'-bisbenzyloxy-2'-hydroxyacetophenone (3.12 g, 6.3 mmol) in ethanol (60 mL) was treated with piperidine (9 mL) and refluxed for 16 h. A yellow solution formed first, and later deposited a yellow precipitate. After 16 h, the reaction was cooled down and the solid collected by filtration and washed copiously with cold ethanol. The solid was further triturated with ethanol at room temperature for 16 h and filtered again to obtain the pure product SR 13178 as a fluffy, crystalline, yellow solid (3.48 g, 74%). TLC: Hexanes: $CH_2Cl_2$ (65:35): $R_f$=0.21; $^1$H NMR (300 MHz, CDCl₃): δ 4.87 (s, 4H, CH₂OPh), 5.11 (m, 6H, CH₂OPh), 6.18 (d, J=2.37 Hz, 1H, 8-H), 6.26 (d, J=2.37 Hz, 1H, 6-H), 6.70 (s, 2H, 2',6'-H), 7.19-7.45 (m, 25H, Ar—H), 7.65 (d, J=15.51 Hz, 1H, CH=CH), 7.78 (d, J=15.45 Hz, 1H, CH=CH), 14.21 (s, 1H, OH); $^{13}$C (75 MHz, CDCl₃): δ 70.38, 71.20, 75.26, 93.07, 95.22, 108.44, 127.10-128.83, 130.84, 135.94, 142.46, 152.92, 161.55, 165.24, 168.18, 192.63. Anal. calcd. for $C_{50}H_{42}O_7$; C, 79.56; H, 5.61; Found: C, 79.47; H, 5.64.

EXAMPLE 5

SYNTHESIS OF 5,7-BIS-BENZYLOXY-2-(3,4,5-TRIS-BENZYLOXY-PHENYL)-CHROMAN-4-ONE (SR 13180)

To a solution of the chalcone SR 13178 (100 mg, 0.15 mmol) in methylene chloride (10 mL) was added 1,3-diazabicycloundecene (DBU) (0.3 mL, 2 mmol) and the red solution was stirred at room temperature for 16 h. 1N hydrochloric acid (50 mL) was added to the reaction mixture and the organic layer separated, washed with water and brine, dried (over MgSO₄) and evaporated to afford the crude product, which was purified by flash column chromatography, eluting with methylene chloride to yield fractions containing pure product. These were evaporated to afford SR 13180 as a light yellow solid (75 mg, 75% yield). TLC: $CH_2C_{12}$: EtOAc (98: 2): $R_f$=0.52; $^1$H NMR (300 MHz, $CDCl_3$): δ 2.72 (dd, J=2.99 and 16.61 Hz, 1H, 3-H equatorial), 2.96 (dd, J=13.19 and 16.54 Hz, 1H, 3-H axial), 5.05 (2s, 4H, $CH_2OPh$), 5.13 (s, 4H, $CH_2OPh$), 5.16 (s, 2H, $CH_2OPh$), 5.29 (dd, J=2.87 and 13.39 Hz, 1H, 2-H), 6.24 (s, 2H, 6,8-H), 6.74 (s, 2H, 2',6'-Ar—H), 7.36-7.58 (m, 25H, Ar—H); $^{13}$C (75 MHz, $CDCl_3$): δ 45.83, 70.37, 70.55, 71.55, 75.31, 79.34, 94.95, 95.36, 106.30, 126.63, 134.32, 135.87, 136.45, 136.96, 153.16, 161.19, 164.80, 164.98, 188.70. Anal. calcd. for $C_{50}H_{42}O_7.0.5 H_2O$, C, 78.18; H, 5.80; Found: C, 77.99; H, 5.74.

EXAMPLE 6

SYNTHESIS OF 5,7-BIS-BENZYLOXY-2-(3,4,5-TRIS-BENZY-LOXY-PHENYL)-CHROMAN-4-OL (SR 13183)

This compound was synthesized by the reduction of SR 13180 as shown in Scheme 3, using the same reaction conditions as that for Example 3 (synthesis of SR 13179).

A solution of the flavanone SR 13180 (2.24 g, 2.97 mmol) in THF (50 mL) and ethanol (20 mL) was treated with sodium borohydride (0.113 g, 2.97 mmol) and refluxed gently for 2 hours. The cooled reaction mixture was evaporated to dryness and redissolved in ethyl acetate. This solution was washed with 1N hydrochloric acid and water, dried (anhydrous $Na_2SO_4$), filtered and evaporated to give the crude product. This was purified by flash column chromatography and the product was eluted with $CH_2Cl_2$/hexanes (9:1). Fractions containing pure product were pooled and evaporated to yield 1.35 g (60%) of pure SR 13183 as a yellow solid. TLC: $CH_2Cl_2$: EtOAc (98:2) $R_f$=0.81; $^1$H NMR (300 MHz, $CDCl_3$): δ 2.17 (m, 1H, 3-H), 2.43 (m, 1H, 3-H), 3.89 (d, 1H, OH), 4.90 (d, 1H, 4-H), 5.00-5.12 (4s, 10H, $OCH_2$), 5.38 (m, 1H, 2-H), 6.21 and 6.29 (2s, 2H, 6,8-Ar—H), 6.76 (s, 2H, 2',6'-Ar—H), 7.30-7.41 (m, 25H, Ar—H). Anal. calcd. for $C_{50}H_{44}O_7$; C, 79.34; H, 5.86; Found: C, 79.41; H, 5.92.

Scheme 4 illustrates the syntheses of SR 13181 and SR 13187, as described in Examples 7 and 8, respectively:

SCHEME 4

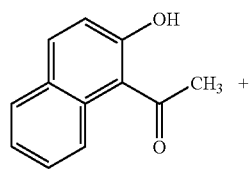

9

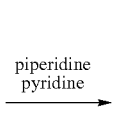

2

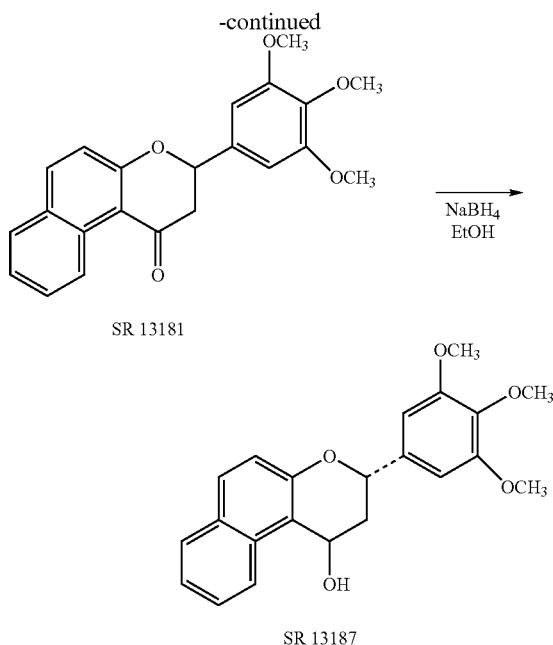

EXAMPLE 7

SYNTHESIS OF 3',4',5'-TRIMETHOXY-B-NAPHTHAFLAVAN-4-ONE (SR 13181)

A solution of 2-hydroxy-1-acetonaphthone 9 (1 g, 5.37 mmol) and 3,4,5-trimethoxybenzaldehyde 2 (1.06 g, 5.37 mmol) in EtOH (50 mL) was treated with piperidine (2 mL) and pyridine (3 mL) and allowed to reflux for 20 h. The cooled reaction mixture was evaporated to dryness and the residue dissolved in methylene chloride (200 mL). The organic solution was washed with 1N hydrochloric acid, water and brine, dried ($MgSO_4$) and evaporated to afford the crude product. This was purified by flash column chromatography, eluting the flavanone SR 13181 with hexanes/ethyl acetate (8:2). Fractions containing the pure product were pooled and evaporated to yield SR 13181 as an off-white solid (1.71 g, 81% yield). TLC: Hexanes: EtOAc (7:3) $R_f$=0.38; $^1$H NMR (300 MHz, $CDCl_3$): δ 2.96 (dd, J=3.03 and 16.54 Hz, 1H, 3-H equatorial), 3.23 (dd, J=13.74 and 16.54 Hz, 1H, 3-H axial), 3.87 and 3.91 (2s, 9H, $OCH_3$), 5.52 (dd, J=3.0 and 13.74 Hz, 1H, 2-H), 6.74 (s, 2H, 2',6'-H), 7.19 (d, 1H, Ar—H), 7.47 (m, 1H, Ar—H), 7.65 (m, 1H, Ar—H), 7.77 (d, 1H, Ar—H), 7.95 (d, 1H, Ar—H), 9.49 (d, 1H, Ar—H); $^{13}$C (75 MHz, $CDCl_3$): δ 45.92, 56.36, 60.92, 79.89, 103.59, 112.70, 118.83, 125.01, 125.94, 128.40, 129.39, 129.76, 131.51, 134.06, 137.59, 153, 67, 163.58, 192.86. Anal. calcd. for $C_{22}H_{20}O_5$; C, 72.51; H, 5.53; Found: C, 72.40; H, 5.58.

EXAMPLE 8

SYNTHESIS OF 3-(3,4,5-TRIMETHOXYPHENYL)-2,3-DIHYDRO-1H-BENZO[F]CHROMEN-1-OL (SR 13187)

This compound was synthesized by the reduction of SR 13181 as shown in Scheme 4, using the same reaction conditions as that for Example 3 (synthesis of SR 13179).

A solution of the flavanone SR 13181 (1.4 g, 3.85 mmol) in ethanol (25 mL) was treated with $NaBH_4$ (110 mg, 2.88 mmol) and stirred at room temperature for 3 h. The reaction mixture was diluted with water, acidified to pH 4 with 1N hydrochloric acid and extracted with ethyl acetate. The organic layer was washed with water and brine, dried (MgSO$_4$) and evaporated to give the crude material. This was purified by flash column chromatography and the pure product was eluted with hexanes/EtOAc (75:25). Fractions containing pure product were pooled and evaporated to give SR 13187 (1.11 g, 78% yield) as a off-white foamy solid. TLC: hexanes: CH$_2$Cl$_2$: EtOAc (3:1:1) R$_f$=0.26; $^1$H NMR (300 MHz, CDCl$_3$): δ 2.55 (m, 1H, 3-H), 2.80 (2s, 1H, 3-H), 3.84 (m, 6H OCH$_3$), 5.45 (m, 1H, 4-H), 5.05 (m, 1H, 2-H), 6.68 (s, 2H, 2',6'-Ar—H), 7.15-8.20 (4m, 6H, Ar—H). Anal. calcd. for C$_{22}$H$_{22}$O$_5$.0.2H$_2$O, C, 71.41; H, 6.10; Found: C, 71.27; H, 6.17.

EXAMPLE 9

SYNTHESIS OF 3-(3,4,5-TRIMETHOXYPHENYL)-2,3-DIHYDRO-BENZO[F]CHROMEN-1-ONE (SR 13182)

mmol) and stirred at room temperature for 6 h. The reaction mixture was diluted with methylene chloride and washed in a separatory funnel with 1N hydrochloric acid, saturated aqueous sodium bicarbonate, water and brine. The organic layer was dried with anhydrous MgSO$_4$, filtered and evaporated to give 0.233 g of crude material, which was purified by flash column chromatography, eluting the product with hexanes/ethyl acetate (8:2). Fractions containing pure product were pooled and evaporated to afford 0.138 g (90%) of SR 13182 as a white solid. TLC: Hexanes: EtOAc: CH$_2$Cl$_2$ (3:1:1) R$_f$=0.28; $^1$H NMR (300 MHz, CDCl$_3$): δ 2.45 (m, 1H, 3-H), 2.90 (m, 1H, 3-H), 3.90 (m, 18H, OCH$_3$), 5.41 (dd, 1H, 2-H), 6.61 (dd, 1H, 4-H), 6.80 (s, 2H, 2',6'-Ar—H), 7.31 (s, 2H, 2'',6''-Ar—H), 7.39-7.51 (m, 4H, Ar—H), 7.80 (m, 1H, Ar—H), 8.28 (m, 1H, Ar—H). Anal. calcd. for C$_{32}$H$_{32}$O$_9$; C, 68.56; H, 5.75; Found: C, 68.39; H, 5.82.

Scheme 6 illustrates the syntheses of SR 13185, SR 13186, and SR 13191, as described in Examples 10 and 11:

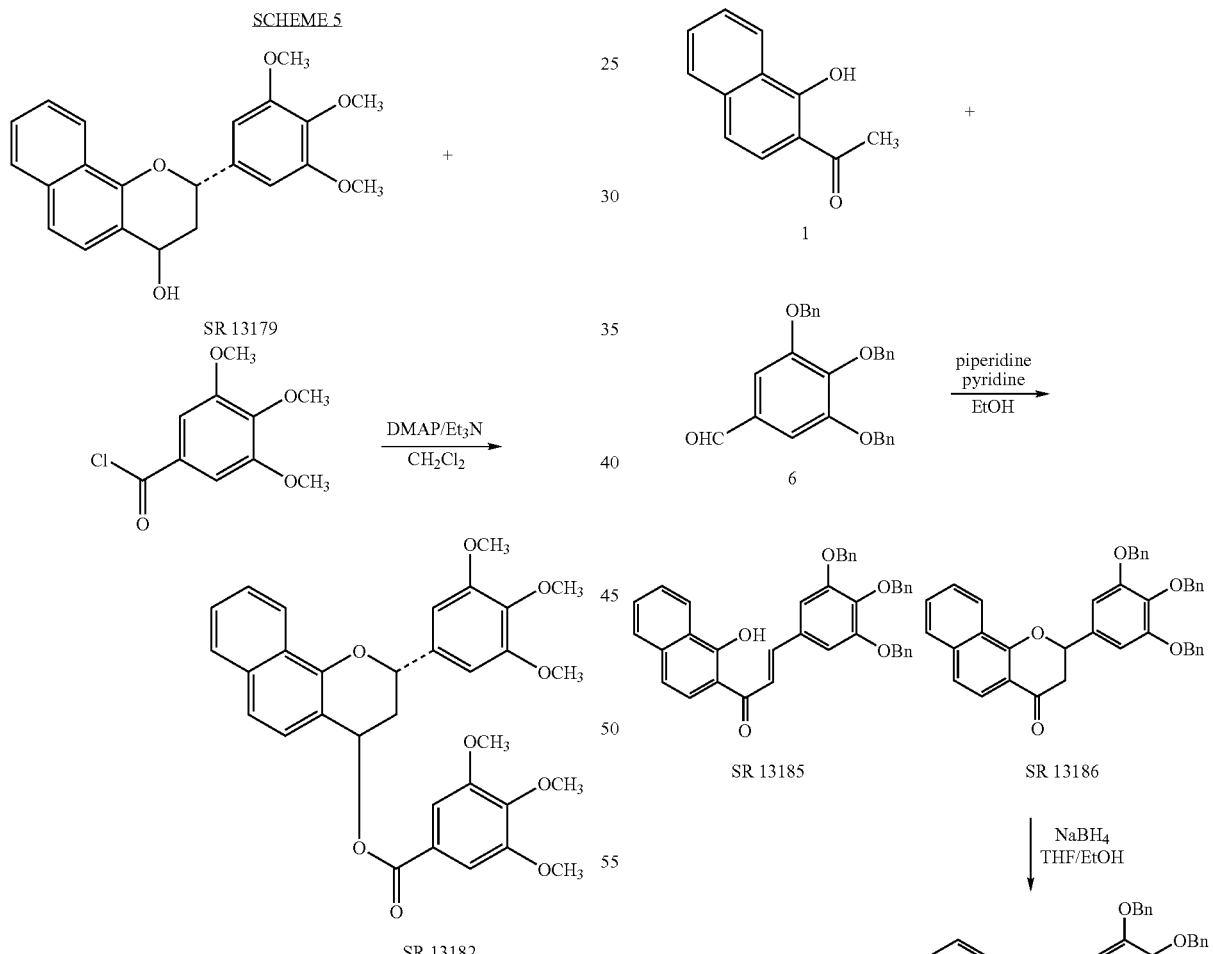

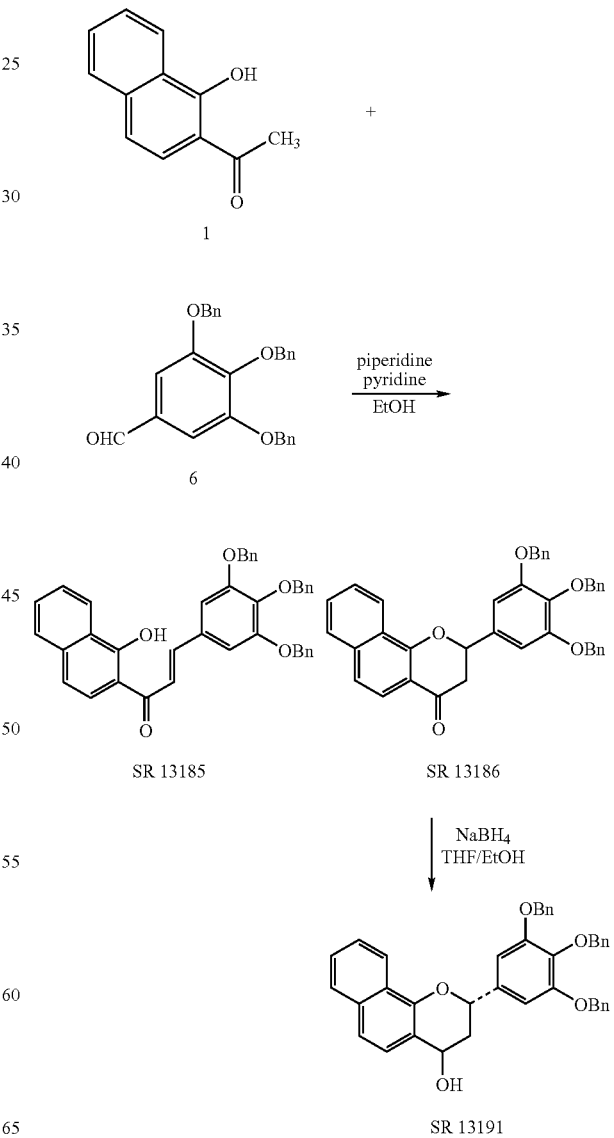

3-(3,4,5-Trimethoxyphenyl)-2,3-dihydro-benzo[F] chromen-1-one (SR 13182) was synthesized according to Scheme 5, as follows: A solution of the alcohol SR 13179 (100 mg, 0.27 mmol) in methylene chloride (10 mL) was treated with triethylamine (0.07 mL, 0.54 mmol) and N,N-dimethyl-4-aminopyridine (DMAP) (33 mg, 0.27 mmol), followed by 3,4,5-trimethoxy-benzoyl chloride (0.088 g, 0.38

EXAMPLE 10

Synthesis of 1-(1-Hydroxy-naphthalen-2-yl)-3-(3,4, 5-tris-benzyloxy-phenyl)-propenone (SR 13185) and 2-(3,4,5-Tris-benzyloxy-phenyl)-2,3-dihydro-benzo[h] chromen-4-one (SR 13186)

Condensation of 1 with 6 as shown in Scheme 6 gave the chalcone SR 13185 as well as the flavanone SR 13186 in one reaction, as follows:

A solution of 1'-hydroxy-2'-acetonaphthone 1 (300 mg, 1.61 mmol) and 3,4,5-tribenzyloxybenzaldehyde 6 (0.68 g, 1.61 mmol) in ethanol (20 mL) was treated with piperidine (1 mL) and pyridine (2 mL) and refluxed for 42 h. The cooled reaction mixture was evaporated to dryness and dissolved in $CH_2Cl_2$. The organic solution was washed with 1N hydrochloric acid, water and brine, dried ($MgSO_4$) and evaporated to give the crude mixture of both products. These were separated stepwise by flash column chromatography, eluting with hexanes/$CH_2Cl_2$ (1:1 to 2:8) to obtain both products as pure fractions. The chalcone SR 13185 was obtained as a yellow solid (80 mg, 9% yield) and the flavanone was obtained as a light yellow solid (225 mg, 24% yield).

SR 13185: TLC: $CH_2Cl_2$: hexanes (6:4) $R_f$=0.35; $^1H$ NMR (300 MHz, $CDCl_3$): δ 5.17 and 5.20 (2s, 6H, $OCH_2Ph$), 6.99 (s, 2H, 2',6'-Ar—H), 7.28-7.87 (m, 22H, ArH, CH=CH), 8.53 (d, 1H, Ar—H) 14.88 (s, 1H, OH); $^{13}C$ (75 MHz, $CDCl_3$): δ 71.67, 75.39, 108.87, 118.17, 119.87, 123.91, 124.57, 125.97, 127.41-130.34, 136.85, 145.04, 153.21, 164.44, 193.01. Anal. calcd. for $C_{40}H_{32}O_5$.$0.1H_2O$, C, 80.82; H, 5.46; Found: C, 80.54; H, 5.59.

SR 13186: TLC: $CH_2Cl_2$: hexanes (6:4) $R_f$=0.13; $^1H$ NMR (300 MHz, $CDCl_3$): δ 2.90 (dd, 1H, 3H), 3.08 (dd, 1H, 3H), 5.11 and 5.15 (2s, 6H, $CH_2OPh$), 5.52 (dd, 1H, 2-H), 6.83 (s, 2H, 2',6'-Ar—H), 7.23-7.50 (m, 18H, Ar—H), 7.90 (d, 1H, Ar—H), 7.87 (d, 1H, Ar—H), 8.19 (d, 1H, Ar—H); $^{13}C$ (75 MHz, $CDCl_3$): δ 44.17, 71.52, 75.34, 80.25, 106.24, 115.58, 121.32, 121.76, 123.69, 124.89, 126.33, 127.46-129.71, 134.33, 136.96, 137.83, 139.00, 153.16, 159.69, 191.42. Anal. calcd. for $C_{40}H_{32}O_5$.$0.3H_2O$, C, 80.33; H, 5.49; Found: C, 80.10; H, 5.55.

EXAMPLE 11

Synthesis of 2-(3,4,5-Tris-benzyloxy-phenyl)-3,4-dihydro-2H-benzo[h]chromen-4-ol (SR 13191)

This compound was synthesized by the reduction of SR 13186 as shown in Scheme 6, using the same reaction conditions as that for Example 3 (synthesis of SR 13179).

A solution of SR 13186 (100 mg, 0.17 mmol) in ethanol (3 mL) and THF (3 mL) was treated with $NaBH_4$ (6.4 mg, 0.17 mmol) and stirred at room temperature for 2.5 h. The reaction mixture was evaporated to dryness and redissolved in ethyl acetate. The organic solution was washed with brine and dried ($MgSO_4$) and evaporated to dryness to afford the crude product, which was purified by flash chromatography. The pure product was eluted with $CH_2Cl_2$/hexanes (97:3) and fractions pooled and evaporated to afford SR 13191 as a white solid (92 mg, 90% yield). TLC: $CH_2Cl_2$ $R_f$=0.30; $^1H$ NMR (300 MHz, $CDCl_3$): δ 2.20 (m, 1H, 3-H), 2.60 (m, 1H, 3-H), 5.09 and 5.12 (2s, 6H, $OCH_2$), 5.20 (m, 2H, 4-H and 2-H), 6.82 (s, 2H, 2',6'-Ar—H), 7.25-8.20 (m, 6H, Ar—H). MS (DCI-$NH_4$): 577 (M+H–$H_2O$), 612 (M+$NH_4$).

Scheme 7 illustrates the syntheses of SR 13188 and SR 13189, as described in Examples 12 and 13:

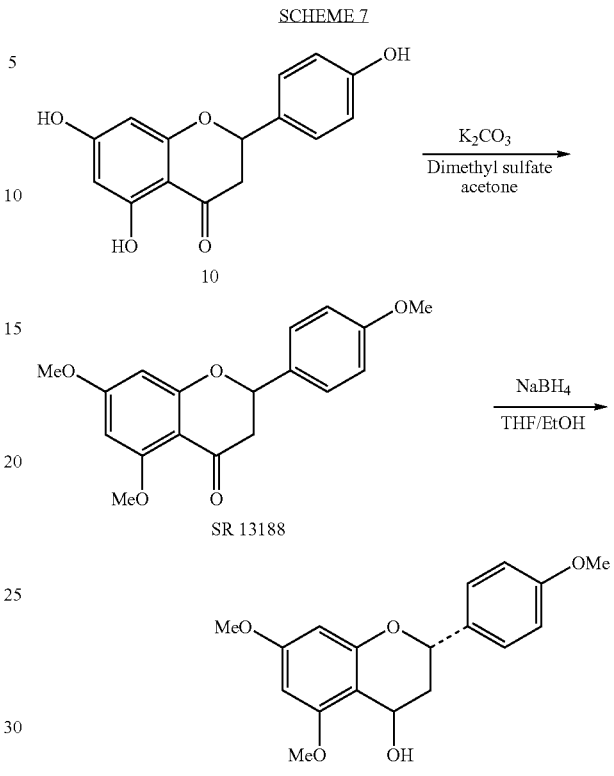

SCHEME 7

EXAMPLE 12

Synthesis of 5,7-Dimethoxy-2-(4-methoxy-phenyl)-chroman-4-one (SR 13188)

SR 13188 was synthesized by methylation of the commercially available flavanone naringenin (10) as shown in Scheme 7, as follows:

Dimethyl sulfate (1.39 mL, 14.7 mmol) was added to a mixture of naringenin 10 (1 g, 3.67 mmol) and $K_2CO_3$ (2.03 g, 14.7 mmol) in acetone (20 mL), and the suspension refluxed for 16 h. The cooled reaction mixture was filtered and evaporated to dryness, redissolved in ethyl acetate and the organic solution was washed with 1N hydrochloric acid, water and brine. The ethyl acetate solution was dried ($MgSO_4$) and evaporated to afford the crude methylated product, which was purified by flash chromatography. The pure product was eluted with methylene chloride and the pooled fractions evaporated to give SR 13188 (0.453 g, 20% yield) as a white solid. TLC: CH2Cl2: EtOAc (95:5) $R_f$=0.30; $^1H$ NMR (300 MHz, $CDCl_3$): δ .2.76 (dd, J=3 and 16.5 Hz, 1H, 3-H), 3.03 (dd, J=13.2 and 16.5 Hz, 1H, 3-H), 3.81 (s, 3H, $OCH_3$), 3.83 (s, 3H, $OCH_3$), 3.89 (s, 3H, $OCH_3$), 5.35 (dd, J=3 and 12.9 Hz, 1H, 4-H), 6.09 (d, 1H, 6-H), 6.13 (d, 1H, 8-H), 6.93 (d, 2H, 2'6'-Ar—H), 7.38 (d, 2H, 3',5'-Ar—H); $^{13}C$ (75 MHz, $CDCl_3$): δ 45.46, 55.37, 55.58, 56.16, 79.02, 93.18, 93.63, 114.21, 127.71, 130.91, 159.97, 165.10, 165.98, 189.36. Anal. calcd. for $C_{18}H_{18}O_5$; C, 68.78; H, 5.77; Found: C, 68.38; H, 5.79.

EXAMPLE 13

Synthesis of 5,7-Dimethoxy-2-(4-methoxy-phenyl)-chroman-4-ol (SR 13189)

SR 13189 was synthesized by reduction of SR 13188 as shown in Scheme 7, using the same reaction conditions as that for Example 3 (synthesis of SR 13179).

A solution of the flavanone SR 13188 (151 mg, 0.48 mmol) in ethanol (5 mL) and THF (2.5 mL) was treated with sodium borohydride (18.2 mg, 0.48 mmol) and stirred at room temperature for 5 h. The reaction mixture was evaporated to dryness and redissolved in ethyl acetate. The organic solution was washed with saturated aqueous $NaHCO_3$ and brine, dried ($MgSO_4$) and evaporated to afford the crude product, which was purified by flash chromatography. The pure product was eluted with $CH_2Cl_2$/hexanes (98:2) and the fractions were evaporated to afford a white solid, which was triturated with hexanes-ether (1:1) and co-evaporated twice to give SR 13189 as a soft white solid (35 mg, 25%). TLC: $CH_2Cl_2$: EtOAc (95:5) $R_f$=0.60; $^1$H NMR (300 MHz, $CDCl_3$): δ 2.25 (m, 1H, 3-H), 2.50 (m, 1H, 3-H), 3.75 (s, 3H, $OCH_3$), 3.82 (s, 3H, $OCH_3$), 3.87 (s, 3H, $OCH_3$), 3.90 (d, 1H, OH), 4.95 (m, 1H, 4-H), 5.23 (m, 1H, 2-H), 6.10 (s, 2H, 6,8-Ar—H), 6.93 (d, 2H, 2',6'-Ar—H), 7.37 (d, 2H, 3',5'-Ar—H); $^{13}$C (75 MHz, $CDCl_3$): δ 37.73, 55.36, 55.39, 55.67, 63.51, 92.35, 94.03, 114.08, 127.76. Anal. calcd. for $C_{18}H_{20}O_5 \cdot 0.1H_2O$, C, 67.95; H, 6.40; Found: C, 67.70; H, 6.44.

EXAMPLE 14

Synthesis of 6-Methoxy-2-(3,4,5-Trimethoxyphenyl)-3,4-dihydro-2H-benzo[h]chromen-4-one (SR 13801)

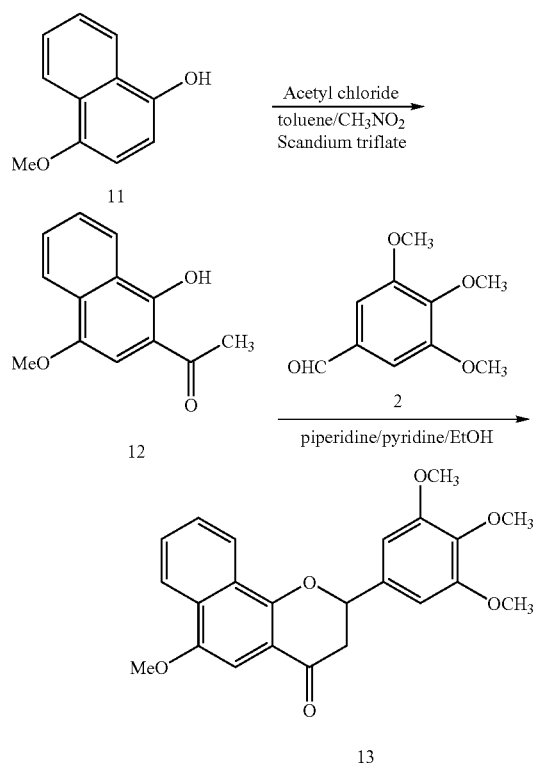

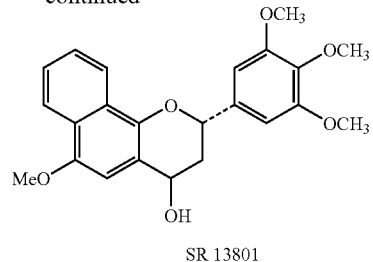

SRI 13801 was synthesized as shown in Scheme 8, by reduction of the flavanone 13 using the same reaction conditions as in Example 3. The flavanone 13 was synthesized from the acetonaphthone 12, which was condensed with trimethoxybenzaldehyde 2 using the same procedure as for the synthesis of SR 13177. The acetonaphthone 12 was obtained by a microwave-assisted Fries acylation of 4-methoxy-1-naphthol 11.

Synthesis of 2-acetyl-4-methoxy-1-naphthol 12. A solution of 4-methoxy-1-naphthol 11 (435 mg, 2.5 mmol) in toluene (5 mL) and nitromethane (0.75 mL) was treated with scandium triflate (61.52 mg, 0.125 mmol) and acetyl chloride (0.195 mL, 2.75 mmol) and irradiated in the microwave reactor (Personal Chemistry, Inc) at a temperature of 170° C. for 5 minutes. The cooled reaction was diluted with methylene chloride and filtered through a small pad of silica gel. The filtrate was evaporated to dryness and purified via flash chromatography, eluting the pure C-acylated product 12 with $CH_2Cl_2$/hexanes (1:1). Pooled fractions were evaporated to afford 12 as a greenish yellow solid (0.388 g, 72% yield). $^1$H NMR (300 MHz, $CDCl_3$): δ 2.69 (s, 3H, $COCH_3$), 3.99 (s, 3H, $OCH_3$), 6.84 (s, 1H, Ar-3-H), 7.80 (m, 2H, Ar—H), 8.10 (d, 1H, Ar—H), 8.21 (d, 1H, Ar—H), 13.76 (s, 1H, OH).

Synthesis of flavanone 13. A solution of the acetonaphthone 12 (1.08 g, 5 mmol) and trimethoxybenzaldehyde (2) (1.08 g, 5.5 mmol) in ethanol (25 mL) was treated with piperidine (3 mL) and pyridine (3 mL) and refluxed for 24 h. On cooling, the product, 13 precipitated out of solution and was collected by filtration and washed with ethanol to yield 488 mg of 13 as the first crop. The filtrate was further purified by flash chromatography and the product eluted with hexanes/$CH_2Cl_2$/EtOAc (6:3:1) to give a light orange solid, which was recrystallized from ethanol to afford an additional 399 mg of a second crop. Combined yield 45%. $^1$H NMR (300 MHz, $CDCl_3$): δ 2.99 (m, 1H, 3-H), 3.19 (m, 1H, 3-H), 3.91, 3.93, 4.03 (3s, 12H, $OCH_3$), 5.57 (m, 1H, 2-H), 6.80 (s, 2H, 2',6'-Ar—H), 7.18 (s, 1H, Ar-5-H) 7.57 (m, 1H, Ar—H), 7.65 (m, 1H, Ar—H), 8.26 (d, 1H, Ar—H), 8.33 (d, 1H, Ar—H).

Synthesis of SR 13801. To a solution of 13 (394 mg, 0.76 mmol) in methanol (15 mL) was added sodium borohydride (30.27 mg, 0.80 mmol) and the solution stirred for 1 h. The reaction mixture was poured into water and extracted with $CH_2Cl_2$. The organic solution was washed with water and brine and dried ($MgSO_4$). Filtration and evaporation of the organic solution gave the crude material, which was purified by recrystallization from methanol to give 184 mg of pure SR 13801 as a white solid (61% yield). $^1$H NMR (300 MHz, $CDCl_3$): δ 2.26 (m, 1H, 3-H), 2.67 (m, 1H, 3-H), 3.88 (m, 9H, $OCH_3$), 4.00 (s, 3H, $OCH_3$), 5.19 (m, 1H, 4-H), 5.25 (m, 1H, 2-H), 6.76 (s, 2H, 2',6'-Ar—H), 6.93 (s, 1H, Ar-5-H), 7.50 (m, 2H, Ar—H), 8.20 (m, 2H, Ar—H).

EXAMPLE 15

SYNTHESIS OF SR 13817

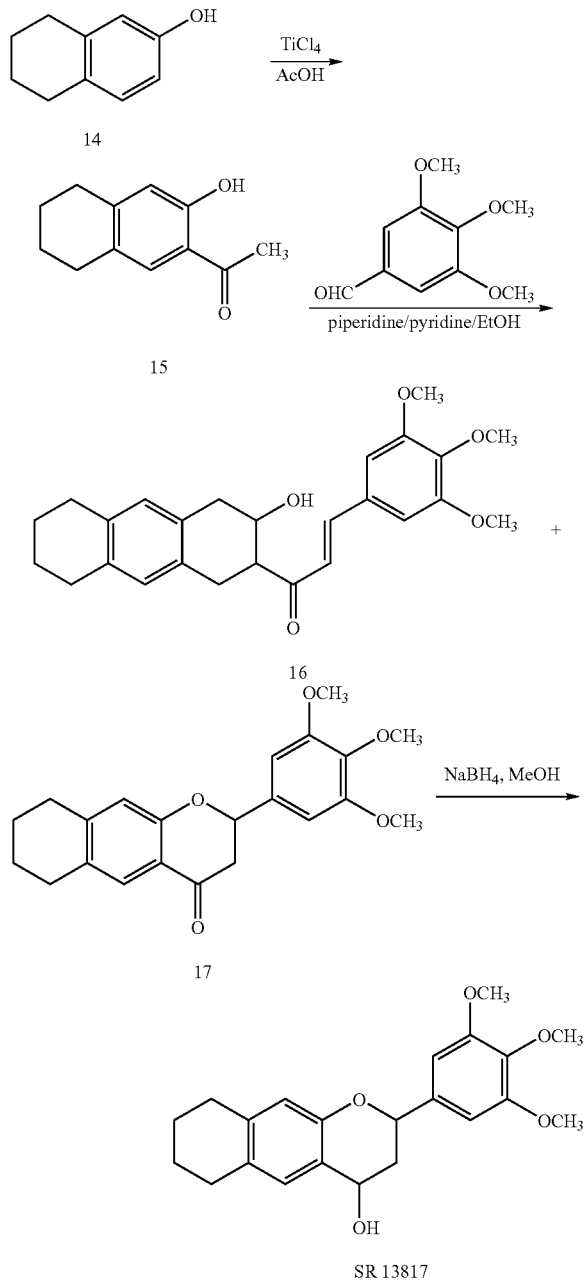

(a) 1-(3-Hydroxy-5,6,7,8-tetrahydronaphthalen-2-yl)ethanone (15)

To 5,6,7,8-tetrahydro-2-naphthol 14 (10 mmol, 1.48 g) placed in a flask flushed with argon at room temperature, was slowly added $TiCl_4$ (11 mmol, 1.2 mL). The resulting dark cherry-colored mixture was stirred at room temperature, and when gas evolution ceased, 15 mmol (1.07 mL) of acetic acid was added to the solid. The resulting thick solution was stirred at room temperature for 15 min, then brought to 120° C. and left to stir at this temperature for an additional hour. The reaction mixture was then cooled to room temperature, diluted with $CH_2Cl_2$ (30 mL) and quenched with $H_2O$ (30 mL). A cloudy solution was obtained which was easily extracted with $CH_2Cl_2$. The organic layer was washed with $H_2O$ (2×30 mL), dried ($Na_2SO_4$), and concentrated under reduced pressure. The crude material was purified by silica gel column chromatography using a mixture of hexanes/EtOAc (95/5) to give 15 as a yellowish solid (1.14 g, 59% yield). mp 70-72° C.; $^1H$ NMR (CDCl$_3$) δ 1.77 (m, 4H), 2.59 (s, 3H), 2.76 (m, 4H), 6.68 (s, 1H), 7.41 (s, 1H), 11.96 (s, 1H); $^{13}C$ NMR (CDCl$_3$) δ 22.87, 23.42, 26,72, 28.82, 30.17, 117.82, 118.21, 128.10, 131.04, 147.71, 160.09, 204.16; IR (KBr, ν cm$^{-1}$) 2934, 1621, 1491, 1344; MS (ESI) 191 (M+1). Anal. Calcd for $C_{12}H_{14}O_2$: C, 75.76; H, 7.42. Found: C, 75.91; H, 7.46.

(b) Synthesis of 16 and 17: A 50 mL round bottom flask was charged with the acetotetrahydronaphthol 2 (10.9 mmol, 2 g), 3,4,5-trimethoxy benzaldehyde (12 mmol, 2.37 g), piperidine (4 mL), pyridine (4 mL) and ethanol (25 mL). The reaction mixture was brought to reflux and left to stir for 18 hours after which the reaction becomes very sluggish. Both chalcone (16) and flavanone (17) were present by TLC, along with some remaining starting material. The mixture was then cooled down to room temperature, diluted with 50 mL of ethyl acetate and 60 mL of 5% HCl. The organic phase was separated, washed with brine, dried over magnesium sulfate then concentrated under reduced pressure. The crude thus obtained was purified by silica gel column chromatography using a mixture of hexane/DCM/EtOAc (6/3/1) to give 362 mg (10% yield) of the chalcone (3) as an orange solid and 1.03 g (26% yield) of the flavanone (4) as a pale yellow.

(2E)-1-(3-hydroxy-5,6,7,8-tetrahydronaphthalen-2-yl)-3-(3,4,5-trimethoxy-phenyl)prop-2-en-1-one (16): $^1H$ NMR (CDCl$_3$): δ 1.80 (m, 4H), 2.78 (m, 4H), 3.91 (s, 3H), 3.95 (s, 6H), 6.74 (s, 1H), 6.89 (s, 2H), 7.49 (d, J=15.2 Hz, 1H,), 7.581 (s, 1H), 7.49 (d, J=15.2 Hz, 1H,), 12.55 (s, 1H, OH). MS (ESI+): 392 (M+Na+1), 305. 2-(3,4,5-trimethoxyphenyl)-2,3,6,7,8,9-hexahydro-4H-benzo[g]chromen-4-one (17): $^1H$ NMR (CDCl$_3$): δ δ 1.80 (m, 4H), 2.80 (m, 4H), 2.84 (dd, J=3, 16.8 Hz, 1H), 3.04 (dd, J=13.2, 16.8 Hz, 1H), 3.86 (s, 3H), 3.89 (s, 6H), 5.35 (dd, J=2.7, 12.9 Hz), 6.69 (s, 2H), 6.78 (s, 1H), 7.63 (s, 1H). $^{13}C$ (75 MHz, CDCl$_3$): δ 22.87, 23.28, 28.71, 30.35, 45.21, 56.36, 56.40, 79.83, 79.95, 103.43, 117.66, 119.10, 127.02, 127.16, 131.30, 134.88, 138.41, 147.52, 153.76, 159.30, 192.20. (ESI+): 391 (M+Na), 369 (M+1), 219, 202.

(c) 5-(4-hydroxy-3,4,6,7,8,9-hexahydro-2H-benzo[g]chromen-2-yl)benzene-1,2,3-trimethoxy (SR 13817): Sodium borohydride (3 mmol, 114 mg) was added to a suspension of the flavanone 17 (2.63 mmol, 970 mg) in methanol (15 mL). The reaction was stirred at room temperature for 15 min after which all flavanone was reduced. The mixture was diluted in ethyl acetate/water, and the organic solution was washed with water and brine and dried (MgSO$_4$). The crude product obtained by evaporation of the ethyl acetate solution, was purified by flash column chromatography and the pure product was eluted with hexanes/ethyl acetate (7:3) to give 846 mg (87% yield) of SR 13817 as a white solid. $^1H$ NMR (300 MHz, CDCl$_3$): δ 1.76-1.78 (m, 4H), 2.04-2.16 (m, 1H), 2.46-2.52 (m, 1H), 2.70-2.73 (m, 4H), 3.85 (s, 3H), 3.88 (s, 6H), 5.02-5.07 (m, 2H), 6.64 (s, 1H), 6.66 (s, 2H), 7.22 (s, 1H). MS: (ESI+): 393 (M+Na).

EXAMPLE 16

IN VITRO DETERMINATION OF GROWTH INHIBITORY ACTIVITY

Compounds of the invention were tested for their ability to inhibit growth in two breast cancer cell lines, MCF-7 (ER+) and MDA-MB-231 (ER−).

The growth inhibition assays were conducted using routine methods. Briefly, the cells were seeded in 24-well plates at a density of 2000 cells per well in 200 µL of water containing growth medium. To each well was added 10 µL of DMSO containing the dissolved test compound; final DMSO concentration in each well was not more than 0.5%. Each test compound was assayed at concentrations of 0.4, 2, 10, and 50 µM. The plates were incubated for eight days, with the media and test solutions replaced every third day. On Day 8, the viable cells were measured by the MTT assay, as described in Mosmann et al. (1983), "Rapid Colorimetric Assay for Cellular Growth and Survival: Application to Proliferation and Cytotoxicity," *J. Immunol. Method.* 65:55-63. The optical density at 575 nm of each test well was measured and compared to that for control wells, and the data used to calculate the percentage of growth inhibition at different concentrations. The $IC_{50}$ value (the concentration of growth inhibitor that results in 50% growth inhibition of the cells in culture relative to control cells not exposed to any growth inhibitor) was determined by plotting dose-response curves.

The calculated $IC_{50}$ values are set forth in Table 1, with the results representing the average of at least two experiments conducted for each compound at each of the four concentrations. As may be seen, a number of the experimental compounds demonstrated growth inhibitory activity against both of the breast cancer cell lines.

TABLE 1

| Compound | GROWTH INHIBITION ($IC_{50}$) (µM) | |
|---|---|---|
| | MCF-7 (ER+) | MDA-MB-231 (ER−) |
| SR 13176 | >50 | 39 |
| SR 13177 | 4.65 | — |
| SR 13178 | 53 | >100 |
| SR 13179 | 1.41 | 3.01 |
| SR 13180 | >50 | >50 |
| SR 13181 | >100 | >100 |
| SR 13182 | >50 | >50 |
| SR 13183 | >100 | 13.62 |
| SR 13185 | 5.08 | 0.562 |
| SR 13186 | 7.32 | 9.84 |
| SR 13187 | 6.29 | — |
| SR 13188 | >50 | >50 |
| SR 13189 | >50 | >50 |
| SR 13191 | 19.90 | >50 |
| SR 13812 | 0.62 | 2.10 |
| SR 13817 | 0.56 | 1.51 |

EXAMPLE 17

IN VITRO DETERMINATION OF GROWTH INHIBITORY ACTIVITY OF SR 13179 IN CANCER CELL LINES

The novel compound SR 13179 was assayed for its ability to inhibit growth in several cancer cell lines. The cell lines studied included breast cancer cell line MCF-7 (ER+); prostate cancer cell lines LNCaP, PC3, and DU145; lung cancer cell line A427; ovarian cancer cell lines IGROV1, OVCAR-3, OVCAR-4, OVCAR-5, OVCAR-8, and SK-OV-3; and colon cancer cell lines COLO 205, HCC-2998, HCT-116, HCT-15, HT29, KM12, AND SW-620.

The growth assays for the breast cancer cell lines were conducted according to the method of Example 16. For the other cell lines, each assay was conducted with continuous exposure to the test compound at four log concentrations for six days, using a sulforhodamine-based protein determination to measure growth inhibition. The results are shown in Table 2.

TABLE 2

GROWTH INHIBITION OF TUMOR CELL LINES BY SR 13179

| Cell Line | $IC_{50}$ (µM) |
|---|---|
| Breast cancer | |
| MCF-7 (ER+) | 1.14 |
| Prostate cancer | |
| LNCaP | 0.21 |
| DU145 | 0.638 |
| PC-3 | 0.289 |
| Ovarian cancer | |
| IGROV1 | 0.281 |
| OVCAR-3 | 0.180 |
| OVCAR-4 | 0.423 |
| OVCAR-5 | 1.36 |
| OVCAR-8 | 0.364 |
| SK-OV-3 | 0.529 |
| Colon cancer | |
| COLO 205 | 0.266 |
| HCC-2998 | 0.278 |
| HCT-116 | 0.310 |
| HCT-15 | 0.270 |
| HT29 | 0.430 |
| KM12 | 0.168 |
| SW-620 | 0.281 |
| Lung cancer | |
| A427 | 0.51 |

As may be seen in the table, potent growth inhibition was demonstrated for all cancer lines studied.

EXAMPLE 18

ACTIVITY OF SR 13179 IN INHIBITING PROLIFERATION AND INDUCING APOPTOSIS IN HUMAN VASCULAR ENDOTHELIAL CELLS

Angiogenesis depends upon the proliferation of vascular endothelial cells. To determine the potential antiangiogenic activity of SR 13179, the compound's ability to inhibit the proliferation of these cells was assayed. Apoptosis was then investigated as a possible mechanism for the antiproliferative activity.

Human vascular endothelial cells taken from umbilical veins (HUVECs) were obtained from Clonetics Corporation (San Diego, Calif.). Growth inhibition was measured quantitatively using the MTT assay as described by Mosmann et al., cited in the previous example.

As shown in FIG. 1, SR 13179 inhibited the growth of HUVECs in a dose-dependent manner. The concentration to inhibit growth by 50% was 0.37 µM. This potent inhibition of vascular endothelial cells by SR 13179 suggests an antiangiogenic component to its antitumor activity.

The antiproliferative mechanism was investigated by assaying for apoptosis using the method of Gavrieli et al. using a Promega (Madison, Wis.) apoptosis detection kit (Gavrieli et al. (1992) *J Cell. Biol.* 119:493-501). Briefly, HUVEC cells were treated with four log concentrations of SR 13179 (1 nM, 10 nM, 100 nM, and 1 µM) and fixed for terminal deoxyribonucleotide transferase-mediated dUTP nick end labeling (TUNEL) assay at 3 h and 6 h. The apoptotic cells were labeled with fluorescent dUTP at DNA strand breaks, and were counterstained with Hoechst 33258 to visualize nuclear morphology. Even at concentrations as low as 10 nM at 3 h, apoptosis was clearly evident as pyknotic nuclei. As shown in Table 3, there was a two to three fold increase in the percentage of detected apoptotic cells three hours after exposure to SR 13179. At six hours, there appeared to be massive apoptosis at higher concentrations of SR 13179, such that the cells were detached and lost during the washing steps. It thus appears that the antiproliferative effect of SR 13179 on vascular endothelial cells is mediated by apoptosis.

TABLE 3

INDUCTION OF APOPTOSIS IN HUVEC CELLS BY SR 13179

| Concentration | Percent apoptosis | |
|---|---|---|
| | 3 h | 6 h |
| Control (no SR 13179) | 6.2 | 7.9 |
| 1 nM | 10.3 | 8.5 |
| 10 nM | 10.3 | cells detached |
| 100 nM | 11.9 | cells detached |
| 1 µM | 16.7 | cells detached |

EXAMPLE 19

ANTIANGIOGENIC ACTIVITY OF SR 13179 IN THE CHICK CHORIOALLANTOIC MEMBRANE (CAM) ASSAY

As some compounds can exhibit in vitro cytotoxic activity to inhibit the proliferation of vascular endothelial cells but do not have in vivo antiangiogenic activity, an in vivo assay for antiangiogenic activity was applied to SR13179. The CAM assay, which is widely applied to evaluate in vivo antiangiogenic activity, was utilized with SR 13179.

The methods used were those of Folkman (Auerbach et al. (1974) *Dev. Biol.* 41:391-394), with some modifications. The test compound was dissolved in saline and methylcellulose, and the embryos dosed once daily for 12-14 days. Blood vessel density of each embryo was measured as the quantitative endpoint. The known antiangiogenic compound medroxyprogesterone acetate (MPA) was used as a positive control.

As may be seen in Table 4, SR 13179 was found to have in vivo antiangiogenic activity equivalent to that of MPA.

TABLE 4

ANTIANGIOGENIC ACTIVITY OF SR 13179 IN THE CAM ASSAY

| Compound | Dose (µg/CAM) | Blood vessel density score | Percent inhibition relative to control |
|---|---|---|---|
| Control (no compound) | — | 10.6 ± 1.7 | — |
| SR 13179 | 11.1 | 4.6 ± 2.2 | 57 |
| MPA | 11.1 | 4.5 ± 2.3 | 58 |

EXAMPLE 20

INDUCTION OF CELL CYCLE ARREST IN LNCaP HUMAN PROSTATE CANCER CELLS

To determine whether SR 13179 exerts its antiproliferative activity by perturbing the cell cycle, the nuclear morphology of LNCaP cells was visualized after treatment with SR 13179. The cells were exposed to the compound for 28 h at concentrations of either 0.5 µM or 1 µM and then stained with the nuclear dye Hoechst 33258. The LNCaP cells clearly showed chromatin condensation characteristic of a prometaphase arrest.

To investigate the mitotic arrest in more detail, flow cytometry was used to study the effect of SR 13179 on cell cycle progression for LNCaP cells. Treatment at concentrations of 2 µM and greater for 24 h caused a two-fold increase in the $G_2/M$ fraction compared with the control and a corresponding decrease in the $G_1$ fraction, indicating cell cycle arrest at $G_2/M$. In a separate experiment with MCF-7 human breast carcinoma cells, treatment with 1 µM SR 13179 for 24 h caused a nearly three-fold increase (compared with untreated control) in the hypodiploid (sub $G_1$) fraction, concomitant with the $G_2/M$ arrest, indicative of apoptosis subsequent to a $G_2/M$ checkpoint.

These experiments demonstrate that SR 13179 arrests the growth of cancer cells at the $G_2/M$ phase of the cell cycle, as mitosis is being initiated.

EXAMPLE 21

IN VITRO DETERMINATION OF GROWTH INHIBITORY ACTIVITY IN LNCaP HUMAN PROSTATE CANCER CELLS

The procedure of Example 20 was used to evaluate the growth inhibitory effect of various compounds of the invention on LNCaP cells. Results are shown in Table 5:

TABLE 5

| Compound | Growth Inhibition ($IC_{50}$) (µM) |
|---|---|
| SR 13179 | 0.21 |
| SR 13177 | 2.52 |
| SR 13187 | 17.69 |
| SR 13188 | 3.34 |
| SR 13191 | 6.58 |

EXAMPLE 22

ANTITUMORIGENIC ACTIVITY OF INTRAPERITONEALLY ADMINISTERED SR 13179 ON HUMAN BREAST CANCER XENOGRAFTS IN NUDE MICE

To evaluate the in vivo activity of novel compound SR 13179 against breast cancer, the compound was administered to female BALB/c nude mice that had been implanted with breast cancer cells. In this experiment, MCF-7 human breast cancer cells ($2.5 \times 10^6$ cells) were implanted subcutaneously in both flanks of each mouse. Two days after cell inoculation, one estradiol pellet (10 µg/pellet) was implanted into each mouse by subcutaneous implantation. When tumor volumes reached 100 mm³ (Day 0), SR 13179 was administered at a dose of 12.5 mg/kg, 25 mg/kg and 50 mg/kg intraperitoneally (i.p.) once a day, as a suspension in 0.5% hydroxypropyl cellulose. Body weights and tumor volumes were measured twice a week for 14 days. The tumor volume was expressed as % of initial tumor size which was designated as 100% on Day 0.

Figure 2:
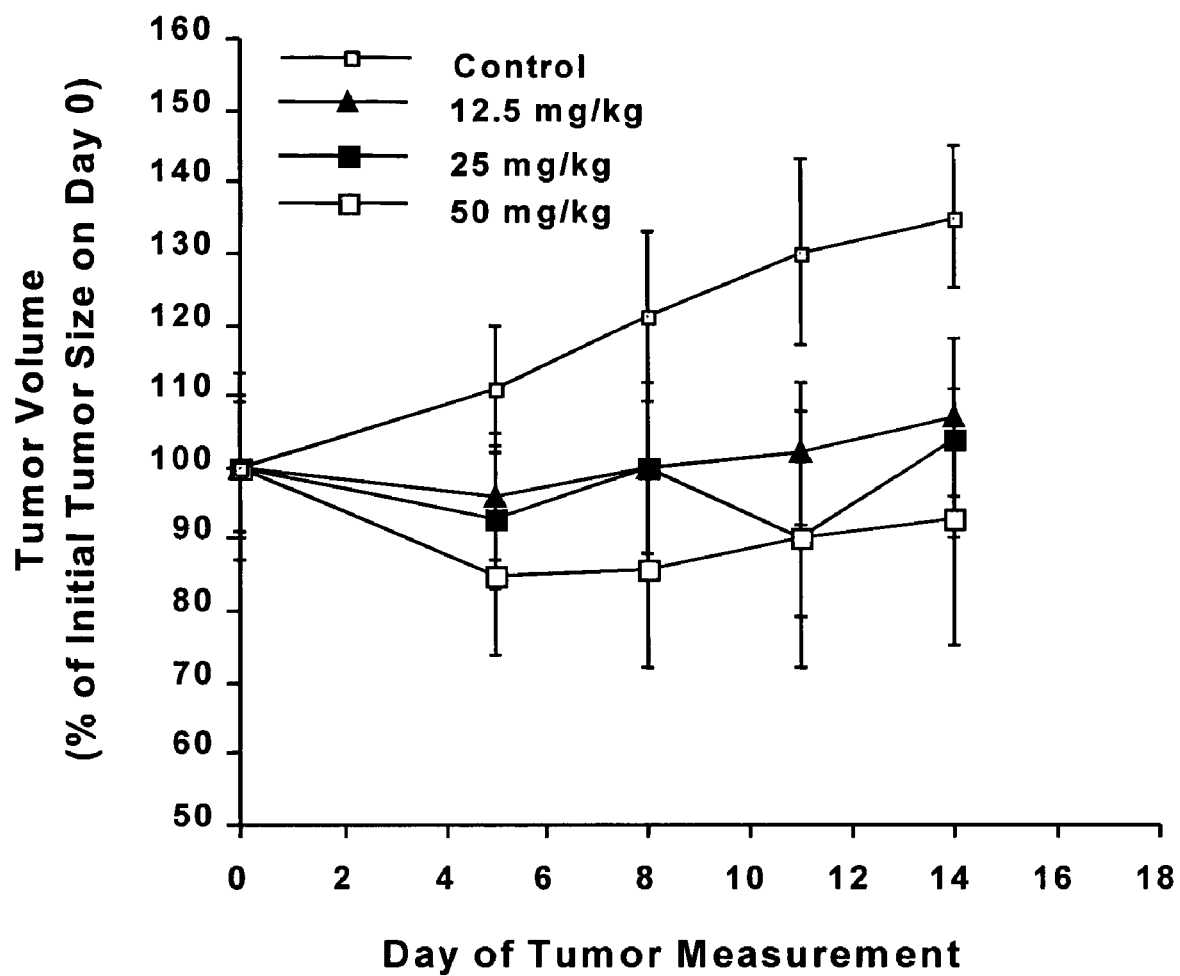
FIG. 2 is a graph illustrating the effect of a compound of the invention (SR 13179) on MCF-7 breast tumor growth in female nude mice, as described in Example 21.

As shown in FIG. 2, mice that received the lowest dose (12.5 mg/kg, day) of SR 13179 showed complete suppression of tumor growth. At the highest dose (50 mg/kg/day), there was even a slight regression in tumor size compared to the size at Day 0. The body weights of the treated mice were unaffected at all doses, and no overt toxicity was observed, indicating that SR 13179 has low systemic toxicity.

EXAMPLE 23

ANTITUMOR ACTIVITY OF ORAL AND I.P. ADMINISTRATION OF SR 13179 ON ADRIAMYCIN-AND CISPLATIN-RESISTANT HUMAN OVARIAN CANCER XENOGRAFTS IN NUDE MICE

Figure 3:
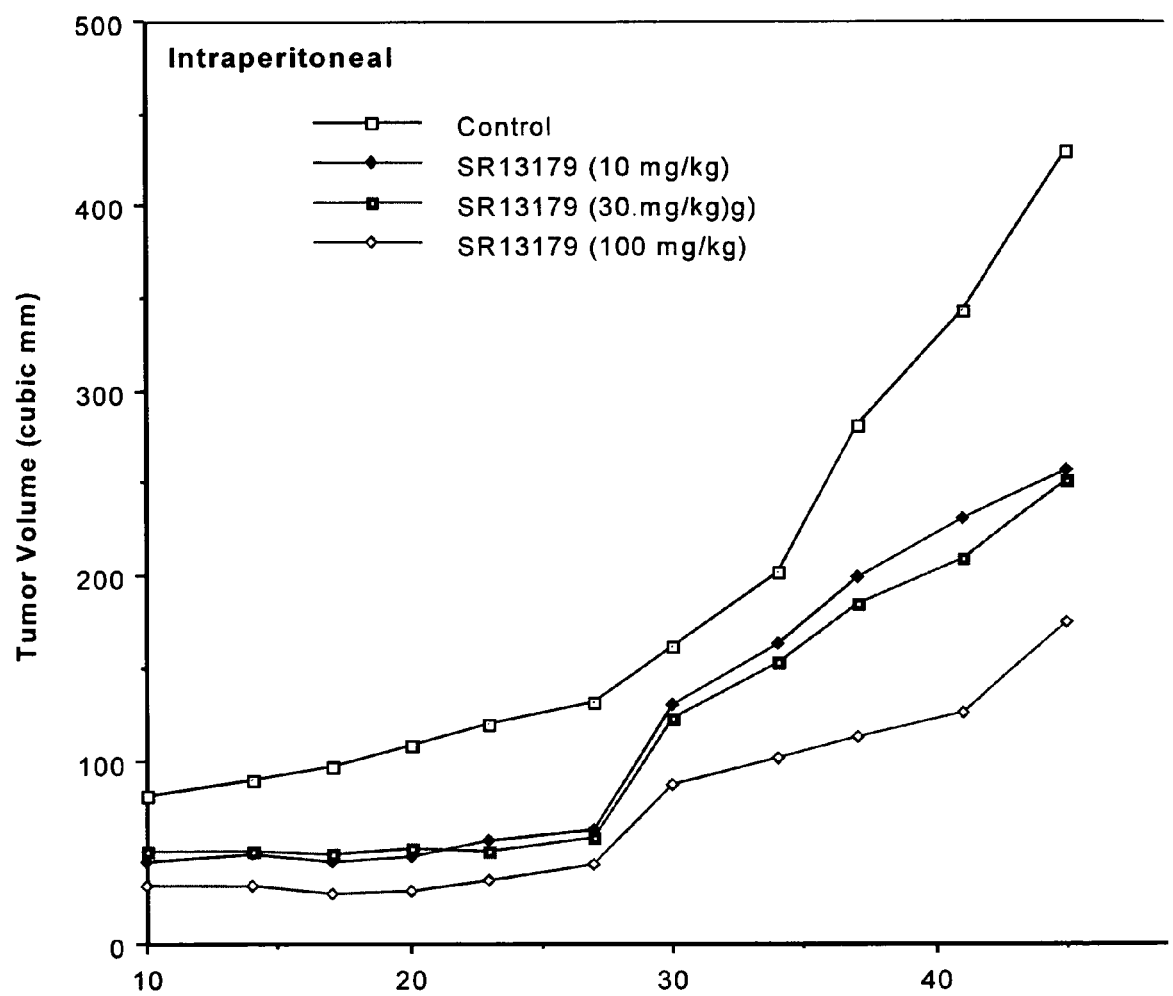
FIGS. 3 and 4 are graphs illustrating the effect of SR 13179 on SKOV-3 cisplatin- and adriamycin-resistant human ovarian tumor cell growth in female nude mice, as described in Example 22.
Figure 4:
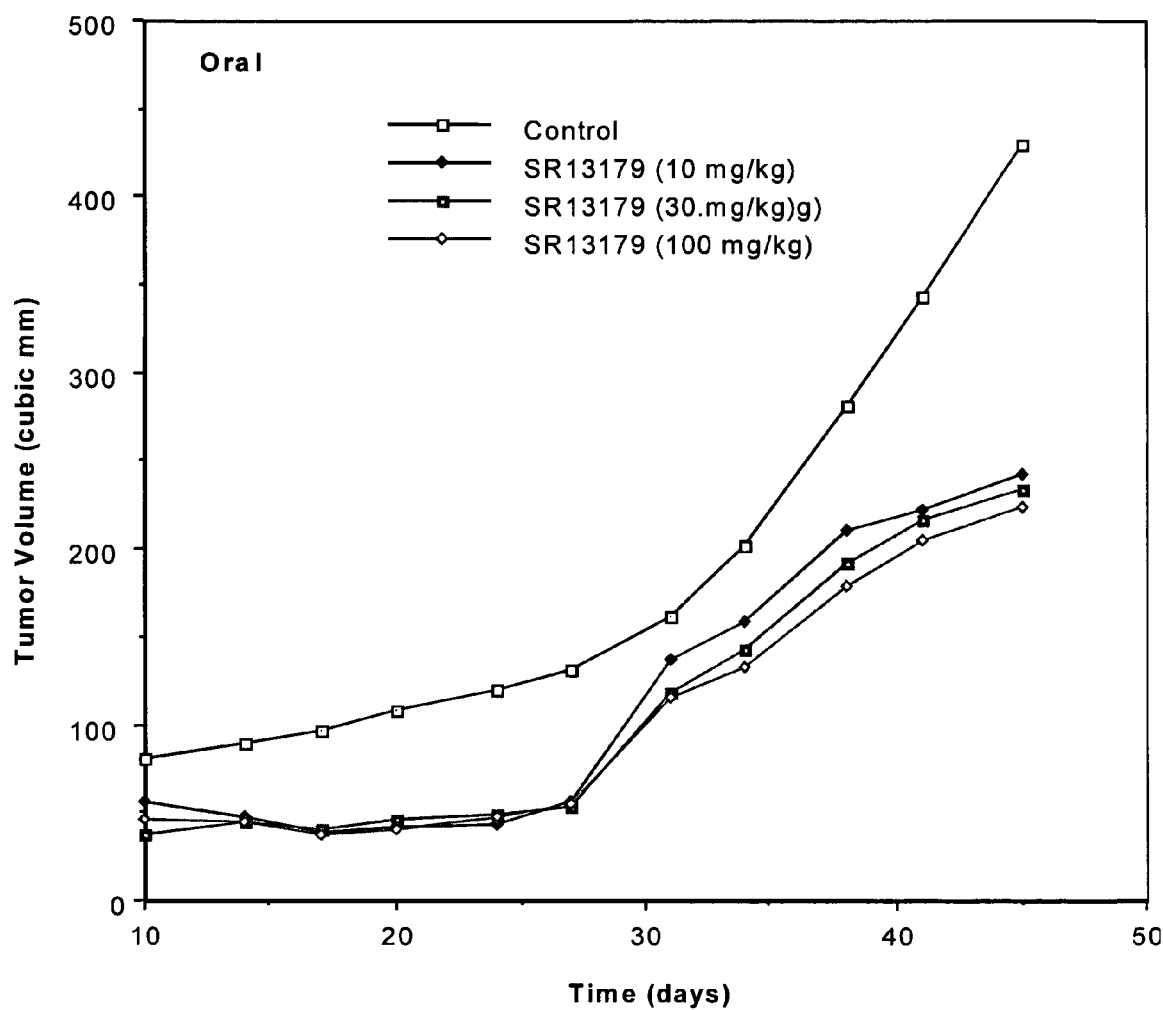

The in vivo antitumor activity of SR 13179 against the highly aggressive adriamycin and cisplatin-resistant human ovarian cancer cell line SKOV-3 was evaluated in nude mice xenografts. The experiment was carried out as follows: Female BALB/c mice were inoculated subcutaneously with the human ovarian cancer SKOV-3 cells on both flanks. SR 13179 was administered to the mice on the same day as tumor cell inoculation, via two routes of administration, orally and intraperitoneally, in three doses of 10 mg/kg, 30 mg/kg and 100 mg/kg, once a day as a suspension in 0.5% hydroxypropylcellulose. Body weights and tumor volumes were measured twice a week. Results. As seen in FIGS. 3 and 4, on Day 10 after tumor inoculation, the tumors in the control group (untreated) reached a 100 mm$^3$ whereas those of the SR 13179-treated groups were smaller by about 50% of the untreated control at Day 10 and tumor growth in the treated groups continued to be significantly inhibited compared to that in the untreated control for the duration of the four-week study. SR 13179 therefore, significantly inhibits the formation of the tumor mass from the implanted tumor cells, and continued to inhibit tumor growth compared to control. The body weights of the treated mice were unaffected at all doses studied.

Accordingly, the novel compounds have shown antiproliferative activity against a number of cancer cell lines, with SR 13179, in particular, exhibiting potent growth inhibition of breast, ovarian, prostate, colon, liver, and lung cancer cells. The compounds have also been established as effective against breast cancer cell lines that express estrogen receptor (ER+) and are stimulated by estrogen, as well as against breast cancer cell lines that do not express estrogen receptor (ER−). In vivo studies in mice indicated complete growth suppression of breast cancer xenografts at nontoxic doses.

The antiangiogenic activity of the compounds has been investigated by studying their effect on human vascular endothelial cells. The proliferation of these cells was potently inhibited, e.g., by SR 13179; further investigation revealed that this inhibition resulted from the induction of apoptosis, which occurred significantly as soon as three hours after exposure to the compound. An in vivo assay for antiangiogenic activity, the chick chorioallantoic membrane (CAM) assay, demonstrated that the antiangiogenic activity of SR 13179 manifests itself in a living organism, and is not simply due to cytotoxicity. The novel compounds of the invention thus display potent anticancer activities and possess considerable advantages over existing chemotherapies. These advantages include efficacy against a wide range of cancers at nontoxic doses.

EXAMPLE 24

INHIBITION OF INVASION OF HUMAN BREAST CANCER CELLS

Cell Culture. MCF-10CA1a cells were cultured in Dulbecco's Modified Eagle Medium (DMEM) supplemented with 5% bovine serum, 2 mM glutamine and 1 mM non-essential amino acids. MDA-MB231 cells were grown in DMEM supplemented with 5% bovine serum. Cells were routinely maintained in a 5% $CO_2$ incubator at 37° C.

General Procedure for Invasion Assay. MCF 10-CA1a or MDA-MB-231 breast cancer cells were treated with 1 or 5 µM of the compound being tested for 8 h. Cells were removed by trypsinizing and tested for their invasiveness by Boyden-chamber invasion assay. In the in vitro invasion/migration assays, a standard Matrigel-based assay, according to the manufacturer's (Becton-Dickinson) protocol, was used. Rehydrated Matrigel and control inserts were added to Falcon TC companion plates containing human fibronectin (30 µg/ml) as chemoattractant. Cellular suspensions ($2 \times 10^4$ cells/ 0.5 ml) were added to individual wells of 24-well chambers (containing either control or Matrigel inserts), and the plates incubated (37° C., 5% $CO_2$) in the presence of the compound being tested or vehicle for an additional 16-18 h. Non-invading or non-migrating cells were removed by scraping the top surfaces of the Matrigel and control inserts, respectively. The invading (or migrating) cells (on the bottom surface) were fixed (3.7% formaldehyde) and stained with Accustain (Sigma). The percent invasion was calculated as mean number of invading cells/the mean number of cells migrating through a control membrane×100.

The in vitro invasion through Matrigel was studied for two human breast cancer lines: MCF-10CA1a, a highly metastatic ER$^+$ line and MDA-MB-231, an ER$^-$ line. Data are presented in Tables 7 and 8, showing that SR13179 possesses anti-invasive metastatic activity. The data show that SR13179 inhibited invasion of MCF-10CA1a cells through Matrigel by 90% at 1 µM. At this concentration, SR13179 inhibited invasion of MDA-MB-231 by about 30% (and by 70% at 5 µM). To rule out a cytotoxic effect in the inhibition of invasion, a concurrent cytotoxicity assay was carried out and the number of viable cells was determined by MTT assay. There was less than 5% decrease in MDA-MB-231 cell viability at 5 µM concentration of SR13179 at 22 h. In the same experiment, a motility experiment was conducted, showing that cell migration was inhibited by about 20%.

These results show that SR 13179 inhibits tumor cell invasion in the highly metastatic breast cancer cell lines MCF-10-CA1a and MDA-MB-231 at doses that are not cytotoxic to cells.

TABLE 6

INVASION AND MIGRATION IN SR 13179-TREATED MCF-10-CA1A CELLS

| | % of Control | |
|---|---|---|
| | DMSO Control | SR 13179 (1 µM) |
| Invasion | 100 | 10 |
| Migration | 100 | 70 |

TABLE 7

INHIBITION OF INVASION OF MDA-MB-231 CELLS

| Concentration of SR 13179 (µM) | Invasion (%) |
| --- | --- |
| 0 | 100 |
| 1 | 60 |
| 5 | 25 |

EXAMPLE 25

MECHANISTIC STUDIES—INHIBITION OF ACTIVITY OF MATRIX METALLOPROTEINASES

The effect of SR 13179 on the activity of MMP-2 (gelatinase) was studied. MCF-10-CA1a cells were treated with 1, 3, and 5 µM SR 13179 in serum-free medium for 48 h. Untreated cells, grown under the same conditions, were used as control. After treatment, supernatants of the cultures were concentrated and subjected to zymography. Zymography of MMP-2 activity indicates that SR 13179 inhibits the enzymatic activity of MMP-2. The inhibition was most pronounced at 5 µM concentration which resulted in >50% inhibition of MMP-2 activity.

The effect of SR 13179 on cell-associated MMP-2 and MMP-9 protein levels was studied. MCF-10-CA1a cells were treated with SR 13179 at 1, 3, or 5 µM concentrations for 48 h. Untreated cells were used as control. Proteins were separated by SDS-Polyacrylamide gel electrophoresis and electrophoretically transformed onto Hybond™ P membrane (Amerhsam Biosciences). Blots were probed with specific antibodies (Santa Cruz Biotechnology Inc.). Western blotting shows that SR 13179 does not affect cell associated levels of cell-associated MMP-2 and MMP-9 protein levels.

EXAMPLE 26

MECHANISTIC STUDIES—INDUCTION OF TIMP-2 EXPRESSION

TIMP-2 is known to play a role in inhibition of tumor invasion and angiogenesis by blocking the activation of pro-MMP-2, a process regulated by complex formation of TIMP-2 with MT1-MMP. However, the antiangiogenic and antitumor effects of TIMP-2 may also occur through MMP-independent mechanisms involving inactivation of growth signaling pathways.

The effects of SR 13179 on the protein expression of TIMP-1, TIMP-2, and membrane-type 1 MMP (MT1-MMP) were studied. SR13179 induced the protein expression of TIMP-2 in a dose- and time-dependent manner. MCF-10-CA1a cells were treated with SR 13179 at 1, 3, or 5 µM concentrations for 48 h, or, alternatively, with 5 mM SR 13179 for 8, 24, or 48 h. Cells were lysed and subjected to Western blotting. The resulting data (see Tables 9 and 10) show that TIMP-2 induction increases with increasing concentration of SR 13179, and that TIMP-2 induction increases with increasing time of exposure to SR 13179. The data also show that compound SR 13179 causes induction of TIMP-2 protein at low doses within 24 h.

The effect of SR13179 on the extracellular levels of TIMP-2 as well as MMP-2 was also investigated. Treatment of MCF-10CA1a cells with SR13179 at 5 µM concentration caused 5- to 8-fold increase in the secreted level of TIMP-2 and a 2-fold decrease in the extracellular level of MMP-2. However, extracellular TIMP-2 protein was always associated with MMP-2 protein, even after the samples were boiled for 10 min and separated under the denaturing conditions of gel electrophoresis. SR13179 had no significant effect on MT1-MMP or TIMP-1 protein levels. Northern blot analysis using total RNA isolated from MCF10CA1a cells treated with 0.5, 1, 3, or 5 µM concentrations of SR13179 as template and a 32p-labeled 600 bp cDNA fragment corresponding to the coding region of human TIMP-2 as probe showed a dose-dependent induction of TIMP-2 mRNA which was mapped at about 1 kb. These results indicated that the effect of SR13179 on TIMP-2 expression occurs at the level of transcription.

In a separate experiment, SR13179 also inhibited p38 MAPK in MCF-7 human breast cancer cell line.

The novel compounds thus induce TIMP-2 protein in highly metastatic breast cancer cell lines, regardless of their hormone receptor status. TIMP-2 can suppress tumor angiogenesis and metastasis through both MMP-dependent and MMP-independent pathways. Induction of TIMP-2 represents a mechanism for inhibiting tumor metastasis and tumor angiogenesis.

TABLE 8

TIME-DEPENDENT INDUCTION OF TIMP-2 PROTEIN BY SR 13179

| Time (h) | Level of TIMP-2 Protein |
| --- | --- |
| 0 | 6.8 |
| 8 | 7.9 |
| 24 | 14.5 |
| 48 | 15.9 |

TABLE 9

CONCENTRATION-DEPENDENT INDUCTION OF TIMP-2 PROTEIN BY SR 13179

| Concentration of SR 13179 (µM) | Level of TIMP-2 Protein |
| --- | --- |
| 0 | 4.9 |
| 1 | 6.8 |
| 3 | 14.6 |
| 5 | 16.2 |

We claim:

1. A method of stimulating the endogenous production of a metalloproteinase inhibitor, comprising administering a compound having the structural formula (III)

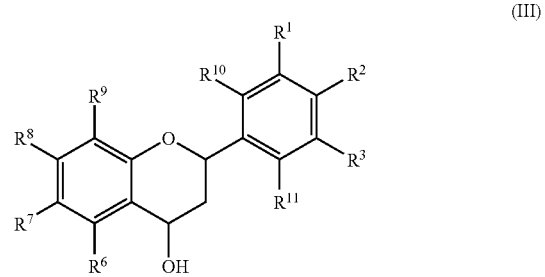

(III)

wherein $R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;

$R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{10}$ and $R^{11}$ are independently selected from the group consisting of hydrogen, hydroxyl, alkyl, alkoxy, and halo, wherein the administering stimulates the endogenous production of a metalloproteinase inhibitor.

2. The method of claim 1, wherein the metalloproteinase inhibitor is TIMP-2, and the metalloproteinase inhibitor is produced in an amount effective to inhibit the breakdown of the extracellular matrix by a metalloproteinase.

3. The method of claim 2, wherein the metalloproteinase is selected from MMP-2, MMP-9, MT1-MMP, and MMP-26.

4. The method of claim 3, wherein the metalloproteinase is selected from MMP-2 and MMP-9.

5. The method of claim 4, wherein the metalloproteinase is MMP-2.

6. The method of claim 1, wherein the compound is useful for treating cancer of the brain, breast, ovary, prostate, lung, kidney or colon.

7. The method of claim 1, wherein the compound is in the form of a pharmaceutically acceptable salt.

8. A method of inhibiting the action of a metalloproteinase involved in the breakdown of the extracellular matrix comprising administering an effective amount of a compound having the structural formula (III)

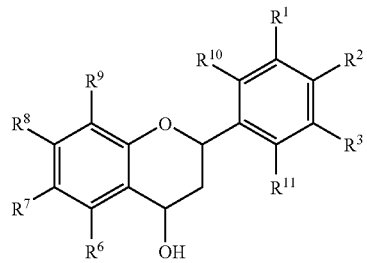

(III)

wherein $R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;

$R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{10}$ and $R^{11}$ are independently selected from the group consisting of hydrogen, hydroxyl, alkyl, alkoxy, and halo, wherein the method inhibits the action of a metalloproteinase.

9. The method of claim 8, wherein the metalloproteinase is selected from MMP2, MMP-9, MT1-MMP, and MMP-26.

10. The method of claim 8, wherein the extracellular matrix comprises collagen.

11. The method of claim 8, wherein the compound is useful for treating cancer of the brain, breast, ovary, prostate, lung, kidney or colon.

12. The method of claim 8, wherein the compound is useful for treating a condition associated with endothelial cell growth or migration.

13. The method of claim 8, wherein the compound is in the form of a pharmaceutically acceptable salt.

14. A method of inhibiting endothelial cell growth or migration, comprising administering a compound having the structural formula (III)

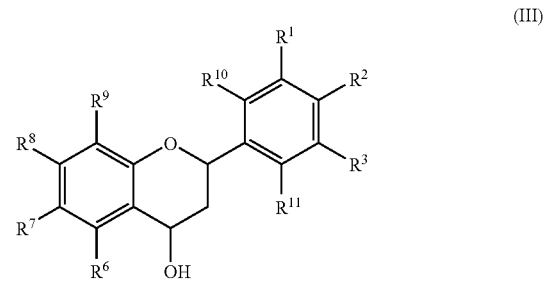

(III)

wherein $R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;

$R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{10}$ and $R^{11}$ are independently selected from the group consisting of hydrogen, hydroxyl, alkyl, alkoxy, and halo, in an amount sufficient to inhibit endothelial cell growth or migration.

15. The method of claim 14, wherein the compound stimulates the endogenous production of a metalloproteinase inhibitor.

16. The method of claim 15, wherein the metalloproteinase inhibitor is TIMP-2.

17. The method of claim 14, wherein the compound inhibits growth-factor signaling in the endothelial cell.

18. The method of claim 14, wherein the compound is useful for treating cancer of the brain, breast, ovary, prostate, lung, kidney or colon.

19. The method of claim 14, wherein the compound is in the form of a pharmaceutically acceptable salt.

20. A method of inhibiting endothelial cell growth or migration comprising contacting a mammalian endothelial cell with a compound having the structure of formula (III)

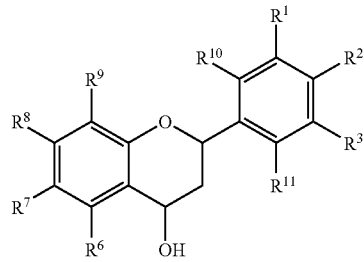

(III)

wherein
- $R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;
- $R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and
- $R^{10}$ and $R^{11}$ are independently selected from the group consisting of hydrogen, hydroxyl, alkyl, alkoxy, and halo,
- in an amount effective to cause inhibition endothelial cell growth or migration.

21. The method of claim 20, wherein the compound stimulates the endogenous production of a metalloproteinase inhibitor.

22. The method of claim 21, wherein the metalloproteinase inhibitor is TIMP-2.

23. The method of claim 20, wherein the compound inhibits growth-factor signaling in the endothelial cell.

24. The method of claim 20, wherein the compound is useful for treating cancer of the brain, breast, ovary, prostate, lung, kidney or colon.

25. The method of claim 20, wherein the compound is in the form of a pharmaceutically acceptable salt.

26. A method of preventing the proliferation of endothelial cells, comprising administering a compound having the structure of formula (III)

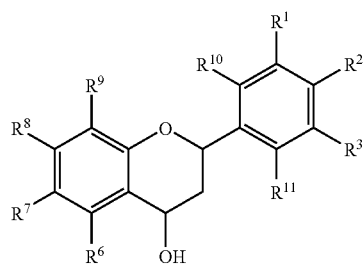

(III)

wherein
- $R^1$, $R^2$ and $R^3$ are independently selected from the group consisting of hydroxyl, halo, sulfhydryl, alkoxy, aryloxy, and aralkyloxy, and further wherein either $R^1$ and $R^2$ or $R^2$ and $R^3$ can be linked to form a cyclic group;
- $R^6$, $R^7$, $R^8$ and $R^9$ are independently selected from the group consisting of hydrogen, alkyl, alkenyl, aryl, aralkyl, alkoxy, aryloxy, and aralkyloxy, providing that $R^6$ and $R^7$, $R^7$ and $R^8$, or $R^8$ and $R^9$, may be linked together to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and
- $R^{10}$ and $R^{11}$ are independently selected from the group consisting of hydrogen, hydroxyl, alkyl, alkoxy, and halo.

27. The method of claim 26, wherein the compound stimulates the endogenous production of a metalloproteinase inhibitor.

28. The method of claim 27, wherein the metalloproteinase inhibitor is TIMP-2.

29. The method of claim 26, wherein the compound is useful for treating cancer of the brain, breast, ovary, prostate, lung, kidney or colon.

30. The method of claim 26, wherein the compound is in the form of a pharmaceutically acceptable salt.

* * * * *